United States Patent
Liu et al.

(10) Patent No.: US 9,126,152 B2
(45) Date of Patent: Sep. 8, 2015

(54) POLYBENZOXAZOLE MEMBRANES FROM SELF-CROSS-LINKABLE AROMATIC POLYIMIDE MEMBRANES

(71) Applicant: UOP LLC, Des Plaines, IL (US)

(72) Inventors: Chunqing Liu, Arlington Heights, IL (US); Zara Osman, Glenview, IL (US); Angela N. Troxell, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/039,545

(22) Filed: Sep. 27, 2013

(65) Prior Publication Data

US 2015/0094500 A1      Apr. 2, 2015

(51) Int. Cl.
 *B01D 29/86* (2006.01)
 *B01D 71/40* (2006.01)
(52) U.S. Cl.
 CPC ..................................... *B01D 71/40* (2013.01)
(58) Field of Classification Search
 CPC ............................... B01D 29/86; C08L 79/04
 USPC ........................................................ 568/917
 See application file for complete search history.

(56) References Cited

U.S. PATENT DOCUMENTS

| | | | |
|---|---|---|---|
| 8,163,071 B2 * | 4/2012 | Lee et al. ........................... | 96/10 |
| 2009/0282982 A1 | 11/2009 | Jung et al. | |
| 2009/0297850 A1 | 12/2009 | Jung et al. | |
| 2010/0133188 A1 | 6/2010 | Liu et al. | |
| 2010/0288701 A1 * | 11/2010 | Zhou et al. .................... | 210/641 |

FOREIGN PATENT DOCUMENTS

| | | |
|---|---|---|
| EP | 2281925 A2 | 2/2011 |
| WO | 2009142433 A2 | 11/2009 |

OTHER PUBLICATIONS

Visser, "Development of asymmetric hollow fiber membranes with tunable gas separation properties", North American Membrane Society, Charleston, South Carolina, Jun. 20-24, 2009.
U.S. Appl. No. 14/039,570, filed Sep. 27, 2013.

* cited by examiner

*Primary Examiner* — Yong Chu
*Assistant Examiner* — Ana Z Muresan

(57) ABSTRACT

A polybenzoxazole (PBO) membrane from a self-cross-linked aromatic polyimide polymer membrane is provided. These membranes are useful in the separation of gas mixtures. The PBO membrane is made by fabricating a self-cross-linkable aromatic polyimide polymer membrane comprising both hydroxyl functional groups and carboxylic acid functional groups; cross-linking the polymer to form a self-cross-linked aromatic polyimide polymer membrane by heating the membrane at 250° to 300° C. under an inert atmosphere; and thermal heating the self-cross-linked aromatic polyimide polymer membrane at a temperature from about 350° to 500° C. under an inert atmosphere to convert the self-cross-linked aromatic polyimide polymer membrane into a PBO membrane. A membrane coating step may be added by coating the selective layer surface of the PBO membrane with a thin layer of high permeability material.

13 Claims, No Drawings

POLYBENZOXAZOLE MEMBRANES FROM SELF-CROSS-LINKABLE AROMATIC POLYIMIDE MEMBRANES

BACKGROUND OF THE INVENTION

This invention relates to a method of making polybenzoxazole (PBO) membranes from self-cross-linkable aromatic polyimide polymer comprising both hydroxyl functional groups and carboxylic acid functional groups and the use of these membranes in separations of gas mixtures and liquid mixtures.

In the past 30-35 years, the state of the art of polymer membrane-based gas separation processes has evolved rapidly. Membrane-based technologies have advantages of both low capital cost and high-energy efficiency compared to conventional separation methods. Membrane gas separation is of special interest to petroleum producers and refiners, chemical companies, and industrial gas suppliers. Several applications have achieved commercial success, including carbon dioxide removal from natural gas and from biogas and enhanced oil recovery, and also in hydrogen removal from nitrogen, methane, and argon in ammonia purge gas streams. For example, UOP's Separex™ cellulose acetate polymeric membrane is currently an international market leader for carbon dioxide removal from natural gas.

Cellulose acetate (CA) glassy polymer membranes are used extensively in gas separation. Currently, such CA membranes are used commercially for natural gas upgrading, including the removal of carbon dioxide. Although CA membranes have many advantages, they are limited in a number of properties including selectivity, permeability, and in chemical, thermal, and mechanical stability. It has been found that polymer membrane performance can deteriorate quickly. A primary cause of loss of membrane performance is liquid condensation on the membrane surface. Condensation can be prevented by providing a sufficient dew point margin for operation, based on the calculated dew point of the membrane product gas. UOP's MemGuard™ system, a regenerable adsorbent system that uses molecular sieves, was developed to remove water as well as heavy hydrocarbons from the natural gas stream, hence, to lower the dew point of the stream. The selective removal of heavy hydrocarbons by a pretreatment system can significantly improve the performance of the membranes. Although these pretreatment systems can effectively perform this function, the cost is quite significant. In some projects, the cost of the pretreatment system was as high as 10 to 40% of the total cost (pretreatment system and membrane system) depending on the feed composition. Reduction of the size of the pretreatment system or even total elimination of the pretreatment system would significantly reduce the membrane system cost for natural gas upgrading. Another factor is that, in recent years, more and more membrane systems have been installed in large offshore natural gas upgrading projects. The footprint is a big constraint for offshore projects. The footprint of the pretreatment system is very high at more than 10 to 50% of the footprint of the entire membrane system. Therefore, removal of the pretreatment system from the membrane system has great economic impact, especially to offshore projects.

Aromatic polybenzoxazoles (PBOs), polybenzthiazoles (PBTs), and polybenzimidazoles (PBIs) are thermally stable ladder-like glassy polymers with flat, stiff, rigid-rod phenylene-heterocyclic ring units. The stiff, rigid ring units in such polymers pack efficiently, leaving very small penetrant-accessible free volume elements that are desirable to provide polymer membranes with both high permeability and high selectivity. These aromatic PBO, PBT, and PBI polymers, however, have poor solubility in common organic solvents, preventing them from being used for making polymer membranes by the most practical solvent casting method.

Thermal conversion of soluble aromatic polyimides containing pendent functional groups ortho to the heterocyclic imide nitrogen in the polymer backbone to aromatic polybenzoxazoles (PBOs) or polybenzthiazoles (PBTs) has been found to provide an alternative method for creating PBO or PBT polymer membranes that are difficult or impossible to obtain directly from PBO or PBT polymers by solvent casting (Tullos et al, MACROMOLECULES, 32, 3598 (1999)). A recent publication in the journal SCIENCE reported high permeability polybenzoxazole polymer membranes in dense film geometry for gas separations (Ho Bum Park et al, SCIENCE 318, 254 (2007)). These polybenzoxazole membranes are prepared from high temperature thermal rearrangement of hydroxy-containing polyimide polymer membranes containing pendent hydroxyl groups ortho to the heterocyclic imide nitrogen. These polybenzoxazole polymer membranes exhibited extremely high $CO_2$ permeability (>100 Barrer) which is at least 10 times better than conventional polymer membranes.

Poly(o-hydroxy amide) polymers comprising pendent phenolic hydroxyl groups ortho to the amide nitrogen in the polymer backbone have also been used for making PBO membranes for separation applications (US 2010/0133188 A1).

One of the components to be separated by a membrane must have a sufficiently high permeance at preferred conditions or extraordinarily large membrane surface areas are required to allow separation of large amounts of material. Permeance, measured in Gas Permeation Units (GPU, 1 GPU=$7.5 \times 10^{-9}$ $m^3$ (STP)/$m^2$ s (kPa)), is the pressure normalized flux and is equal to permeability divided by the skin layer thickness of the membrane. Commercially available polymer membranes, such as cellulose acetate and polysulfone membranes, have an asymmetric structure with a thin dense selective layer of less than 1 µm. The thin selective layer provides the membrane high permeance representing high productivity. Therefore, it is highly desirable to prepare asymmetric PBO membranes with high permeance for separation applications. One such type of asymmetric hollow fiber PBO membrane has been recently disclosed by Park et al. (US 2009/0297850 A1) and Visser et al. (Abstract on "Development of asymmetric hollow fiber membranes with tunable gas separation properties" at NAMS 2009 conference, Jun. 20-24, 2009, Charleston, S.C., USA). The asymmetric hollow fiber PBO membranes disclosed by Park et al. and Visser et al. were obtained from o-hydroxyl substituted polyimide asymmetric hollow fiber membranes via thermal rearrangement. However, Visser et al. found that the high temperature thermally rearranged asymmetric hollow fiber PBO membranes had low gas permeances (equivalent to a dense selective layer thickness of >5 µm). The low gas permeance is because the fiber shrank and the porous substructure collapsed during thermal rearrangement at temperatures higher than 300° C. Therefore, much more research is still required to reduce the excessive densification of the porous membrane substructure of asymmetric o-hydroxyl substituted polyimide membranes during thermal rearrangement at elevated temperature to make asymmetric PBO membranes.

Park et al. also disclosed asymmetric hollow fiber PBO membranes obtained from o-hydroxyl substituted polyamic acid asymmetric hollow fiber membranes via thermal rearrangement (WO 2009142433 and US 2009/0282982 A1).

The present invention provides a method of making polybenzoxazole (PBO) membranes from self-cross-linkable aromatic polyimide polymer comprising both hydroxyl functional groups and carboxylic acid functional groups and methods of using these membranes.

DETAILED DESCRIPTION OF THE INVENTION

The present invention generally relates to a method of making PBO membranes from self-cross-linkable aromatic polyimide polymer comprising both hydroxyl functional groups and carboxylic acid functional groups. The present invention also relates to the use of PBO membranes for gas, vapor, and liquid separations.

The present invention provides a method for the production of a PBO membrane by: 1) fabricating a self-cross-linkable aromatic polyimide polymer membrane from the self-cross-linkable aromatic polyimide polymer comprising both hydroxyl functional groups and carboxylic acid functional groups; 2) cross-linking the self-cross-linkable aromatic polyimide polymer membrane to form the self-cross-linked aromatic polyimide polymer membrane by heating the membrane at 250° C. to 300° C. under an inert atmosphere, such as argon, nitrogen, or vacuum; 3) thermal heating the self-cross-linked aromatic polyimide polymer membrane at a temperature from about 350° to 500° C. under an inert atmosphere, such as argon, nitrogen, or vacuum to convert the self-cross-linked aromatic polyimide polymer membrane into a PBO membrane. In some cases, a membrane coating step is added after step 3) by coating the selective layer surface of the PBO membrane with a thin layer of high permeability material such as a polysiloxane, a fluoro-polymer, a thermally curable silicone rubber, or a UV radiation curable epoxy silicone.

The advantage of using self-cross-linkable aromatic polyimide polymer comprising both hydroxyl functional groups and carboxylic acid functional groups to prepare PBO membrane in the present invention is to prevent the densification of skin layer and substructure during PBO conversion at a temperature between 350° to 500° C. Skin layer and substructure collapse during PBO conversion from traditional aromatic polyimide polymer comprising hydroxyl functional groups and without carboxylic acid functional groups at a temperature between 350° to 500° C. resulted in significantly increased effective separation layer thickness and therefore significantly reduced membrane permeance. The glass-rubber transition temperature (Tg) of the traditional aromatic polyimide polymer comprising hydroxyl functional groups and without carboxylic acid functional groups is below the PBO conversion temperature, which will result in substructure collapse. However, the self-cross-linked aromatic polyimide polymer described in the present invention has a $T_g$ well above its decomposition temperature. The formation of the self-cross-linked aromatic polyimide polymer membrane in the present invention via heating the self-cross-linkable aromatic polyimide polymer membrane at <300° C., which is below the $T_g$ of the self-cross-linkable aromatic polyimide polymer, prevents the densification of skin layer and substructure during PBO conversion at a temperature between 350° to 500° C.

The term "self-cross-linkable aromatic polyimide polymer" in the present invention refers to an aromatic polyimide polymer comprising both carboxylic acid functional groups and hydroxyl functional groups wherein the carboxylic acid functional groups can react with the hydroxyl functional groups via heating. The term "self-cross-linked aromatic polyimide polymer membrane" in the present invention refers to an aromatic polyimide polymer membrane comprising self-cross-linked aromatic polyimide polymer that comprises covalent ester bonds formed from esterification reaction between carboxylic acid functional groups and hydroxyl functional groups.

The self-cross-linkable aromatic polyimide polymer used for the preparation of PBO membrane described in the present invention comprises both hydroxyl functional groups and carboxylic acid functional groups. The self-cross-linkable aromatic polyimide polymer and the self-cross-linkable aromatic polyimide polymer membrane used for the preparation of PBO membrane described in the present invention comprise a plurality of repeating units of formula (I), wherein formula (I) comprises carboxylic acid functional groups and hydroxyl functional groups, and wherein the carboxylic acid functional groups can react with the hydroxyl functional groups via covalent ester bonds at 250° to 300° C. to form self-cross-linked aromatic polyimide polymer described in the present invention comprising a plurality of repeating units of formula (II). The self-cross-linked aromatic polyimide polymer and the self-cross-linked aromatic polyimide polymer membrane used for the preparation of PBO membrane described in the present invention comprise aromatic polyimide polymer chain segments where at least part of these polymer chain segments are cross-linked to each other through direct covalent ester bonds. The formation of the covalent ester bonds among the aromatic polyimide polymer chains via the self-cross-linking of the self-cross-linkable aromatic polyimide polymer comprising both carboxylic acid functional groups and hydroxyl functional groups at 250° to 300° C. results in self-cross-linked aromatic polyimide polymer with a $T_g$ well above its decomposition temperature. The self-cross-linked aromatic polyimide polymer membrane is converted into an a PBO membrane by thermal rearrangement at a temperature from about 350° to 500° C. under an inert atmosphere, such as argon, nitrogen, or vacuum. The heating time for this heating step is in a range of about 30 seconds to 2 hours. A more preferred heating time is from about 30 seconds to 1 hour. The PBO membrane prepared from the self-cross-linkable aromatic polyimide polymer membrane described in the present invention showed significantly higher permeability than the self-cross-linkable aromatic polyimide polymer membrane and the self-cross-linked aromatic polyimide polymer membrane for a variety of gas separation applications such as $CO_2/CH_4$, $H_2/CH_4$, and $He/CH_4$ separations. For example, a PBO membrane prepared from the self-cross-linkable poly[2,2'-bis-(3,4-dicarboxyphenyl)hexafluoropropane dianhydride-3,3'-dihydroxy-4,4'-diamino-biphenyl-3,5-diaminobenzoic acid]polyimide (abbreviated as poly(6FDA-HAB-DBA)) membrane via heating at 450° C. has a high $CO_2$ permeance of 210 Barrers and $CO_2/CH_4$ selectivity of 25.9 for $CO_2/CH_4$ separation. This PBO membrane also has a high $H_2$ permeance of 337.1 Barrers and $H_2/CH_4$ selectivity of 41.5 for $H_2/CH_4$ separation.

The self-cross-linkable aromatic polyimide polymer used for the preparation of PBO membrane described in the present invention comprises a formula (I):

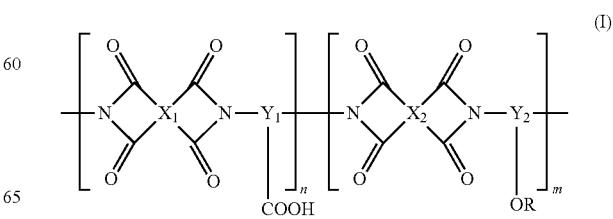

wherein $X_1$ and $X_2$ are selected from the group consisting of

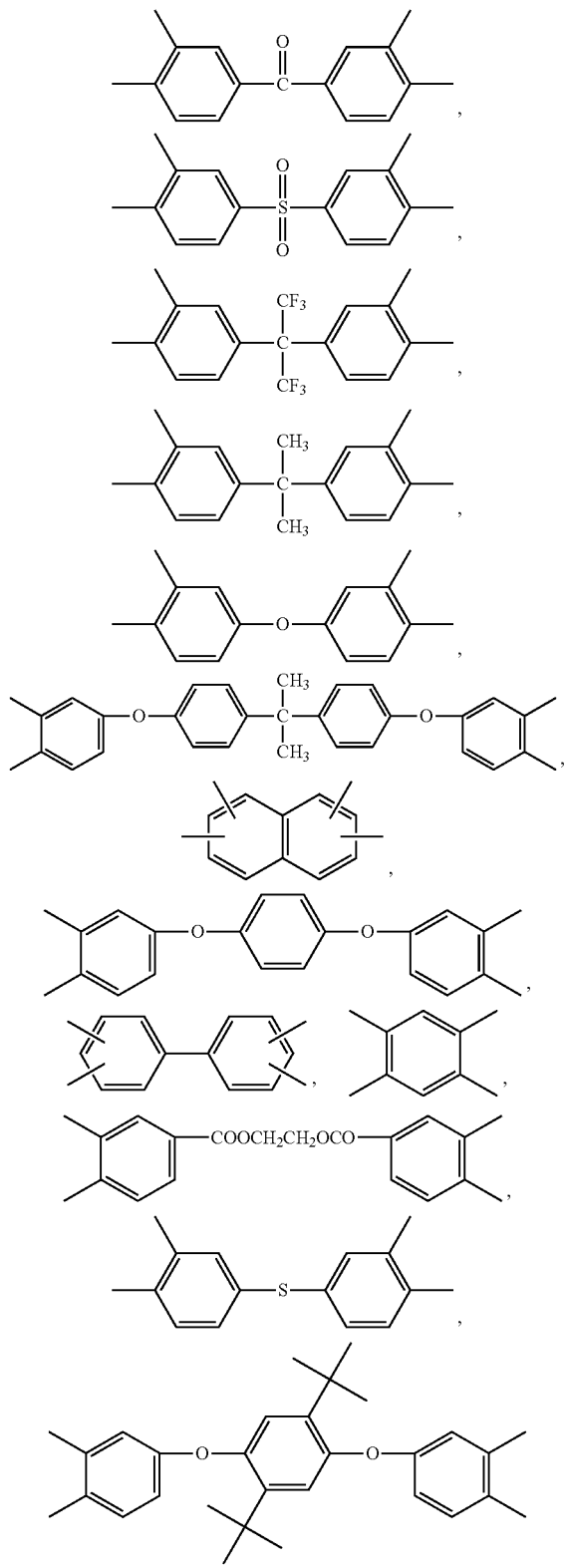

and mixtures thereof, respectively; $X_1$ and $X_2$ are the same or different from each other; $Y_1$—COOH is selected from the group consisting of

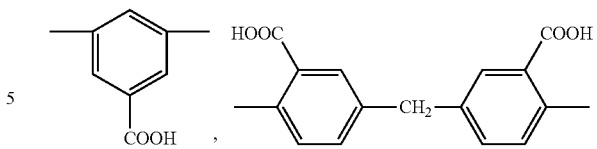

and mixtures thereof; $Y_2$—OR is selected from the group consisting of

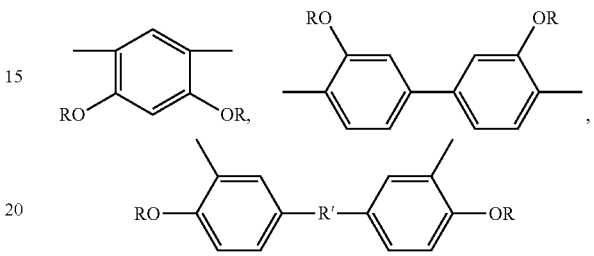

and mixtures thereof, and —R is selected from the group consisting of —H and a mixture of —H and —COCH$_3$, and —R'— is selected from the group consisting of

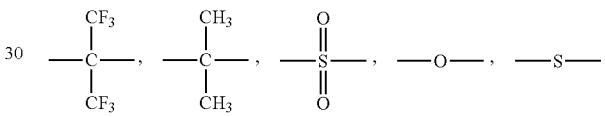

and mixtures thereof; n and m are independent integers from 2 to 500; the molar ratio of n/m is in a range of 1:1 to 1:20.

The self-cross-linkable aromatic polyimide polymer comprising both hydroxyl functional groups and carboxylic acid functional groups used for the preparation of PBO membrane of the invention may be selected from the group consisting of poly(3,3',4,4'-diphenylsulfone tetracarboxylic dianhydride-3,5-diaminobenzoic acid-3,3'-dihydroxy-4,4'-diamino-biphenyl)polyimide derived from a polycondensation reaction of 3,3',4,4'-diphenylsulfone tetracarboxylic dianhydride with a mixture of 3,5-diaminobenzoic acid and 3,3'-dihydroxy-4,4'-diamino-biphenyl; poly(3,3',4,4'-benzophenone tetracarboxylic dianhydride-pyromellitic dianhydride-3,5-diaminobenzoic acid-3,3'-dihydroxy-4,4'-diamino-biphenyl) polyimide derived from a polycondensation reaction of 3,3',4,4'-benzophenone tetracarboxylic dianhydride and pyromellitic dianhydride with 3,5-diaminobenzoic acid and 3,3'-dihydroxy-4,4'-diamino-biphenyl; poly(3,3',4,4'-benzophenone tetracarboxylic dianhydride-3,5-diaminobenzoic acid-3,3'-dihydroxy-4,4'-diamino-biphenyl)polyimide derived from a polycondensation reaction of 3,3',4,4'-benzophenone tetracarboxylic dianhydride with 3,5-diaminobenzoic acid and 3,3'-dihydroxy-4,4'-diamino-biphenyl; poly[2,2'-bis-(3,4-dicarboxyphenyl)hexafluoropropane dianhydride-3,5-diaminobenzoic acid-3,3'-dihydroxy-4,4'-diamino-biphenyl]polyimide derived from the polycondensation reaction of 2,2'-bis-(3,4-dicarboxyphenyl)hexafluoropropane dianhydride with a mixture of 3,5-diaminobenzoic acid and 3,3'-dihydroxy-4,4'-diamino-biphenyl; poly[2,2'-bis-(3,4-dicarboxyphenyl)hexafluoropropane dianhydride-2,2-bis(3-amino-4-hydroxyphenyl)-hexafluoropropane-3,5-diaminobenzoic acid] derived from a polycondensation reaction of 2,2'-bis-(3,4-dicarboxyphenyl)hexafluoropropane dianhydride with a mixture of 2,2-bis(3-amino-4-hydroxyphenyl)-hexafluoropropane and 3,5-diaminobenzoic acid; poly[3,3',4,4'-benzophenonetetracarboxylic dianhydride-2,2-bis(3-amino-4-hydroxyphenyl)-hexafluoropropane-3,5-diaminobenzoic acid] derived from a polycondensation reaction of 3,3',4,4'-benzophenonetetracarboxylic dianhydride with a mixture of 2,2-bis(3-amino-4-hydroxyphenyl)-hexafluoropropane and 3,5-diaminobenzoic acid; poly[4,4'-oxydiphthalic anhydride-2,2-bis(3-amino-4-hydroxyphenyl)-hexafluoropropane-3,5-diaminobenzoic acid] derived from a polycondensation reaction of 4,4'-oxydiphthalic anhydride with a mixture of 2,2-bis(3-amino-4-hydroxyphenyl)-hexafluoropropane and 3,5-diaminobenzoic acid; poly[3,3',4,4'-diphenylsulfone tetracarboxylic dianhydride-2,2-bis(3-amino-4-hydroxyphenyl)-hexafluoropropane-3,5-diaminobenzoic acid] derived from a polycondensation reaction of 3,3',4,4'-diphenylsulfone tetracarboxylic dianhydride with a mixture of 2,2-bis(3-amino-4-hydroxyphenyl)-hexafluoropropane and 3,5-diaminobenzoic acid; poly[2,2'-bis-(3,4-dicarboxyphenyl)hexafluoropropane dianhydride-3,3',4,4'-benzophenonetetracarboxylic dianhydride-2,2-bis(3-amino-4-hydroxyphenyl)-hexafluoropropane-3,5-diaminobenzoic acid] derived from a polycondensation reaction of 2,2'-bis-(3,4-dicarboxyphenyl) hexafluoropropane dianhydride and 3,3',4,4'-benzophenonetetracarboxylic dianhydride with a mixture of 2,2-bis(3-amino-4-hydroxyphenyl)-hexafluoropropane and 3,5-diaminobenzoic acid; poly[4,4'-oxydiphthalic anhydride-2,2-bis(3-amino-4-hydroxyphenyl)-hexafluoropropane-3,3'-dihydroxy-4,4'-diamino-biphenyl-3,5-diaminobenzoic acid] derived from a polycondensation reaction of 4,4'-oxydiphthalic anhydride with a mixture of 2,2-bis(3-amino-4-hydroxyphenyl)-hexafluoropropane, 3,3'-dihydroxy-4,4'-diamino-biphenyl and 3,5-diaminobenzoic acid; poly[3,3',4,4'-benzophenonetetracarboxylic dianhydride-2,2-bis(3-amino-4-hydroxyphenyl)-hexafluoropropane-3,3'-dihydroxy-4,4'-diamino-biphenyl-3,5-diaminobenzoic acid] derived from a polycondensation reaction of 3,3',4,4'-benzophenonetetracarboxylic dianhydride with a mixture of 2,2-bis(3-amino-4-hydroxyphenyl)-hexafluoropropane, 3,3'-dihydroxy-4,4'-diamino-biphenyl, and 3,5-diaminobenzoic acid.

The self-cross-linked aromatic polyimide polymer formed from the self-cross-linkable aromatic polyimide polymer described in the present invention comprises a plurality of repeating units of formula (II):

wherein $X_1$ and $X_2$ are selected from the group consisting of

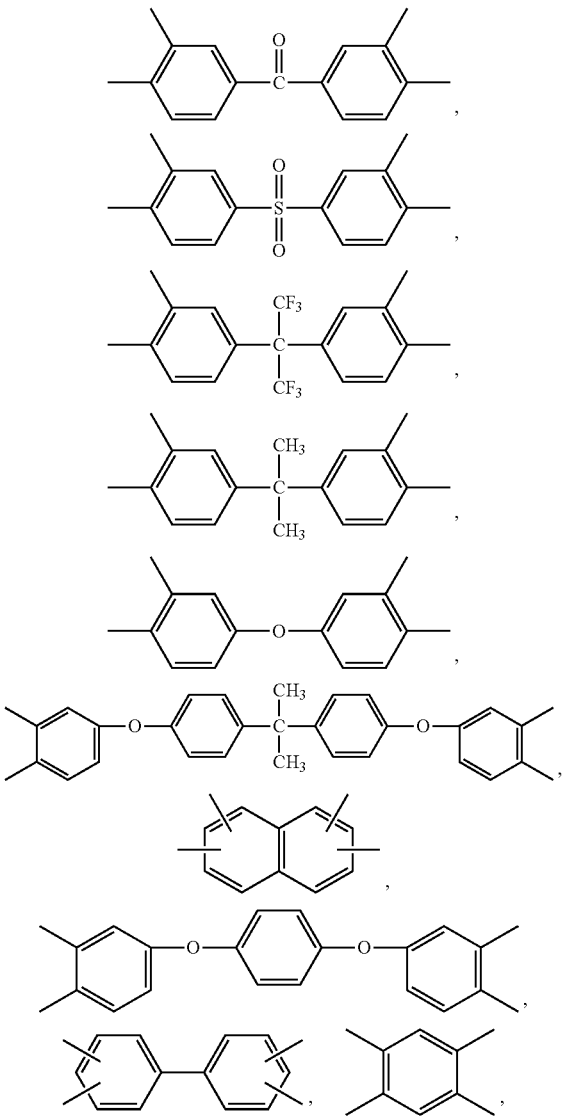

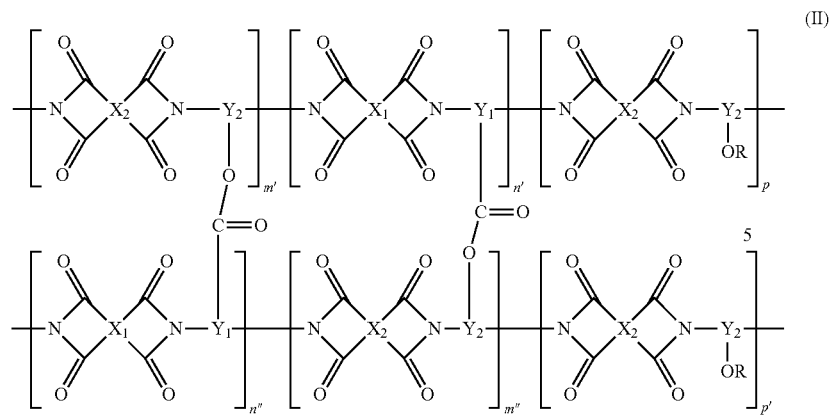

-continued

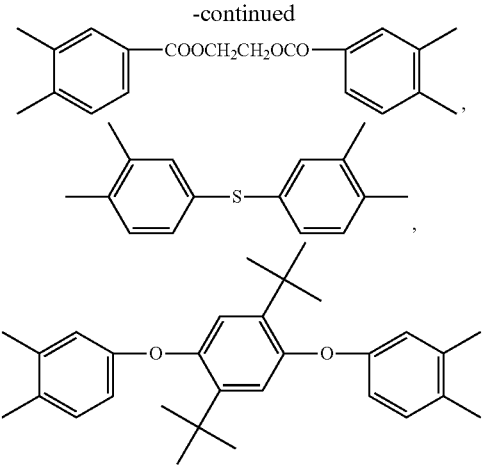

and mixtures thereof, respectively; $X_1$ and $X_2$ are the same or different from each other; $Y_1$—CO— is selected from the group consisting of

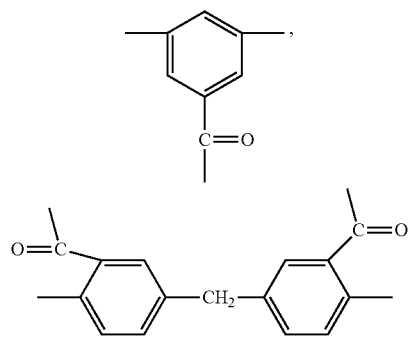

and mixtures thereof; $Y_2$—O— is selected from the group consisting of

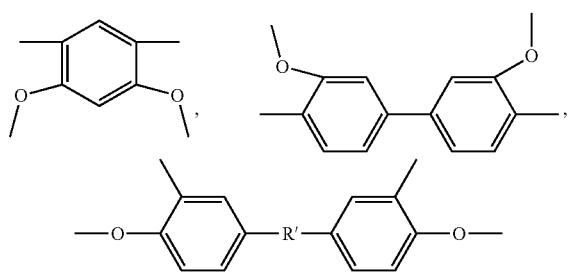

and mixtures thereof, and —R'— is selected from the group consisting of

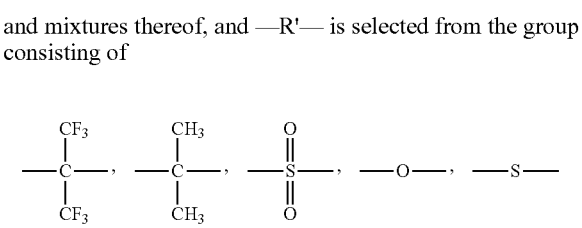

and mixtures thereof; $Y_2$—OR is selected from the group consisting of

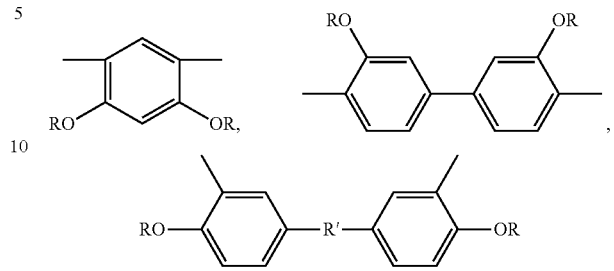

and mixtures thereof, and —R— is selected from the group consisting of —H, and a mixture of —H and —COCH$_3$, and —R'— is selected from the group consisting of

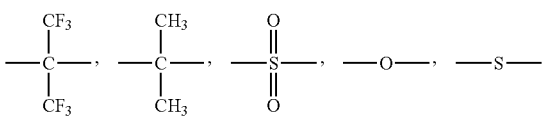

and mixtures thereof; n', n", m', m", p, and p' are independent integers from 2 to 500; the molar ratio of n'/(m'+p) is in a range of 1:1 to 1:20; the molar ratio of n"/(m"+p') is in a range of 1:1 to 1:20.

The self-cross-linkable aromatic polyimide polymer used for the preparation of PBO membrane described in the present invention has a weight average molecular weight in the range of 10,000 to 1,000,000 Daltons, preferably between 70,000 to 500,000 Daltons.

The polybenzoxazole polymer in the polybenzoxazole membrane made from the self-cross-linkable aromatic polyimide polymer in the present invention comprises the repeating units of a formula (III), wherein said formula (III) is:

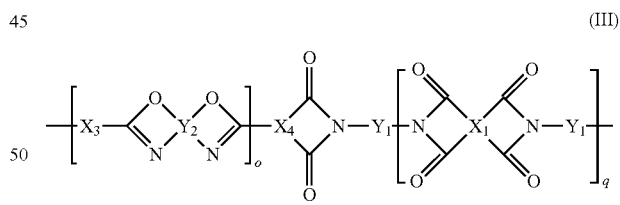

(III)

wherein $X_1$ is selected from the group consisting of

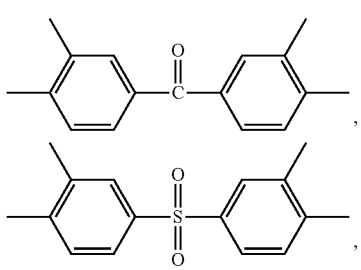

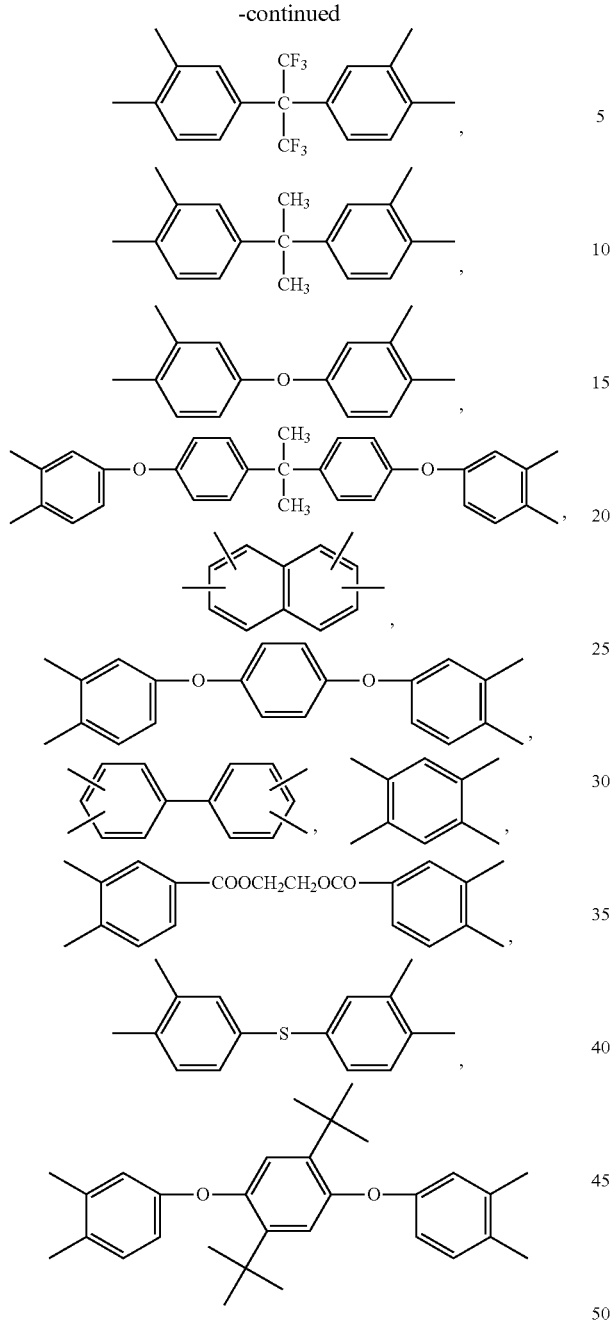
and mixtures thereof; wherein $X_3$ is selected from the group consisting of
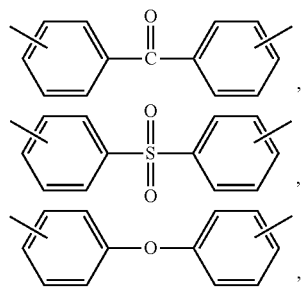
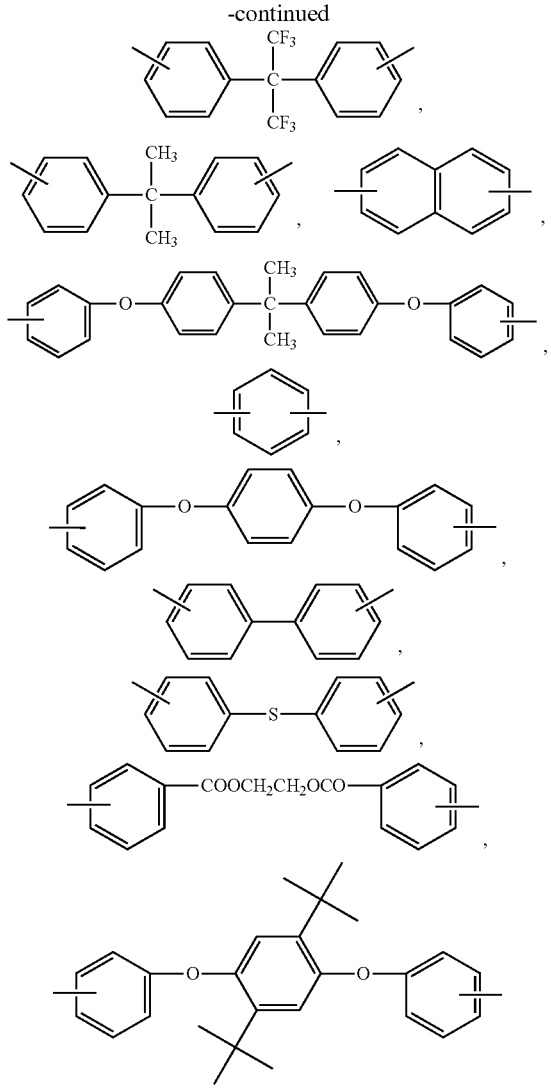
and mixtures thereof; wherein $X_4$ is selected from the group consisting of
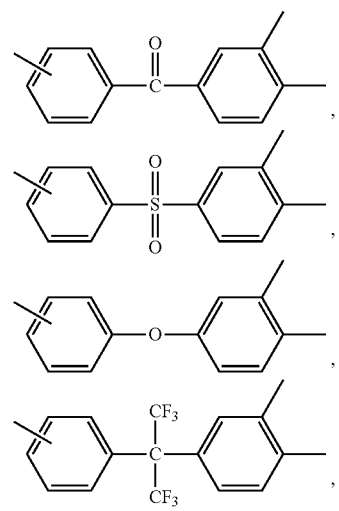

-continued

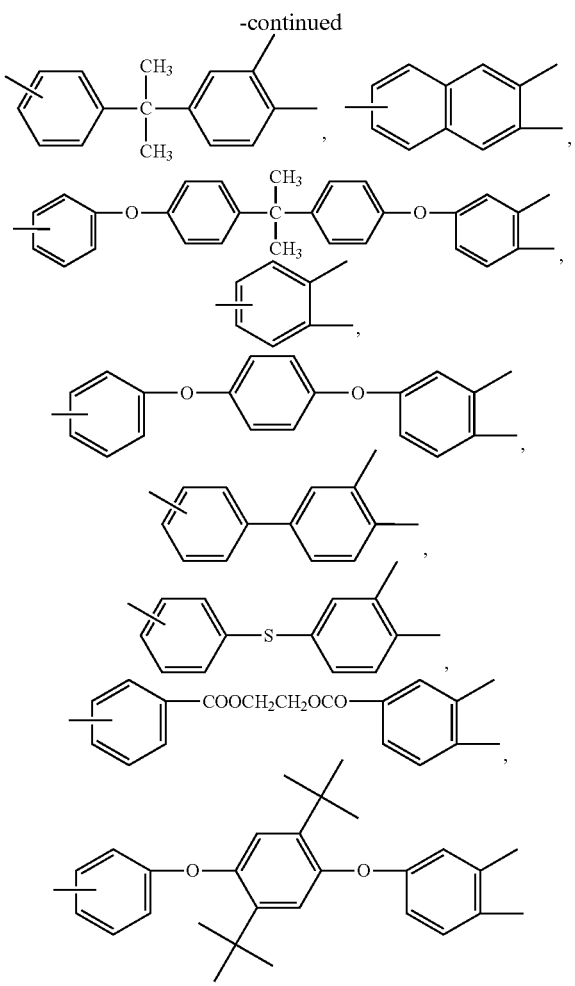

and mixtures thereof; $Y_1$ is selected from the group consisting of

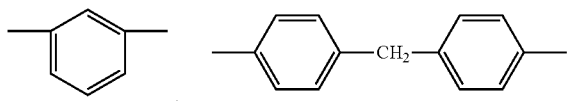

and mixtures thereof; $Y_2$ is selected from the group consisting of

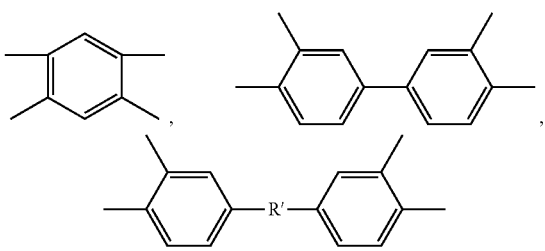

and mixtures thereof, and —R'— is selected from the group consisting of

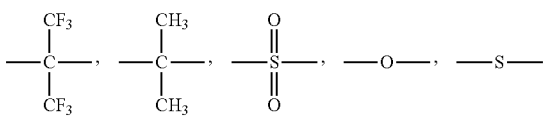

and mixtures thereof; o and q are independent integers from 2 to 500.

In some cases a membrane post-treatment step can be added after the formation of the PBO polymer membrane with the application of a thin layer of a high permeability material such as a polysiloxane, a fluoro-polymer, a thermally curable silicone rubber, or a UV radiation curable epoxy silicone. The coating fills the surface pores and other imperfections comprising voids (see U.S. Pat. No. 4,230,463; U.S. Pat. No. 4,877,528; and U.S. Pat. No. 6,368,382).

The self-cross-linkable aromatic polyimide polymer membrane and the PBO membrane made from the self-cross-linkable aromatic polyimide polymer described in the present invention can be fabricated into any convenient geometry such as flat sheet (or spiral wound), tube, or hollow fiber.

The invention provides a process for separating at least one gas from a mixture of gases using the PBO membrane made from the self-cross-linked aromatic polyimide polymer membrane described in the present invention, the process comprising: (a) providing a PBO membrane made from the self-cross-linked aromatic polyimide polymer membrane described in the present invention which is permeable to said at least one gas; (b) contacting the mixture on one side of the PBO membrane made from the self-cross-linked aromatic polyimide polymer membrane described in the present invention to cause said at least one gas to permeate the membrane; and (c) removing from the opposite side of the membrane a permeate gas composition comprising a portion of said at least one gas which permeated said membrane.

The PBO membrane made from the self-cross-linked aromatic polyimide polymer membrane described in the present invention is especially useful in the purification, separation or adsorption of a particular species in the liquid or gas phase. In addition to separation of pairs of gases, the PBO membrane made from the self-cross-linked aromatic polyimide polymer membrane described in the present invention may, for example, be used for the desalination of water by reverse osmosis or for the separation of proteins or other thermally unstable compounds, e.g. in the pharmaceutical and biotechnology industries. The PBO membrane made from the self-cross-linked aromatic polyimide polymer membrane described in the present invention may also be used in fermenters and bioreactors to transport gases into the reaction vessel and transfer cell culture medium out of the vessel. Additionally, the PBO membrane made from the self-cross-linked aromatic polyimide polymer membrane described in the present invention may be used for the removal of microorganisms from air or water streams, water purification, ethanol production in a continuous fermentation/membrane pervaporation system, and in detection or removal of trace compounds or metal salts in air or water streams.

The PBO membrane made from the self-cross-linked aromatic polyimide polymer membrane described in the present invention is especially useful in gas separation processes in air purification, petrochemical, refinery, and natural gas industries. Examples of such separations include separation of volatile organic compounds (such as toluene, xylene, and acetone) from an atmospheric gas, such as nitrogen or oxygen and nitrogen recovery from air. Further examples of such separations are for the separation of He, $CO_2$ or $H_2S$ from natural gas, $H_2$ from $N_2$, $CH_4$, and Ar in ammonia purge gas streams, $H_2$ recovery in refineries, olefin/paraffin separations such as propylene/propane separation, xylene separations, iso/normal paraffin separations, liquid natural gas separations, $C_2$+ hydrocarbon recovery. Any given pair or group of gases that differ in molecular size, for example nitrogen and oxygen, carbon dioxide and methane, hydrogen and methane or carbon monoxide, helium and methane, can be separated using the PBO membrane made from the self-cross-linked aromatic polyimide polymer membrane described in the present invention. More than two gases can be removed from a third gas. For example, some of the gas components which can be selectively removed from a raw natural gas using the PBO membrane made from the self-cross-linked aromatic polyimide polymer membrane described herein include carbon dioxide, oxygen, nitrogen, water vapor, hydrogen sulfide, helium, and other trace gases. Some of the gas components that can be selectively retained include hydrocarbon gases. When permeable components are acid components selected from the group consisting of carbon dioxide, hydrogen sulfide, and mixtures thereof and are removed from a hydrocarbon mixture such as natural gas, one module, or at least two in parallel service, or a series of modules may be utilized to remove the acid components. For example, when one module is utilized, the pressure of the feed gas may vary from 275 kPa to about 2.6 MPa (25 to 4000 psi). The differential pressure across the membrane can be as low as about 70 kPa or as high as 14.5 MPa (about 10 psi or as high as about 2100 psi) depending on many factors such as the particular membrane used, the flow rate of the inlet stream and the availability of a compressor to compress the permeate stream if such compression is desired. Differential pressure greater than about 14.5 MPa (2100 psi) may rupture the membrane. A differential pressure of at least 0.7 MPa (100 psi) is preferred since lower differential pressures may require more modules, more time and compression of intermediate product streams. The operating temperature of the process may vary depending upon the temperature of the feed stream and upon ambient temperature conditions. Preferably, the effective operating temperature of the membranes of the present invention will range from about −50° to about 150° C. More preferably, the effective operating temperature of the PBO membrane made from the self-cross-linked aromatic polyimide polymer membrane of the present invention will range from about −20° to about 100° C., and most preferably, the effective operating temperature of the membranes of the present invention will range from about 25° to about 100° C.

The PBO membrane made from the self-cross-linked aromatic polyimide polymer membrane described in the present invention are also especially useful in gas/vapor separation processes in chemical, petrochemical, pharmaceutical and allied industries for removing organic vapors from gas streams, e.g. in off-gas treatment for recovery of volatile organic compounds to meet clean air regulations, or within process streams in production plants so that valuable compounds (e.g., vinylchloride monomer, propylene) may be recovered. Further examples of gas/vapor separation processes in which the PBO membrane made from the self-cross-linked aromatic polyimide polymer membrane described in the present invention may be used are hydrocarbon vapor separation from hydrogen in oil and gas refineries, for hydrocarbon dew pointing of natural gas (i.e. to decrease the hydrocarbon dew point to below the lowest possible export pipeline temperature so that liquid hydrocarbons do not separate in the pipeline), for control of methane number in fuel gas for gas engines and gas turbines, and for gasoline recovery. The PBO membrane made from the self-cross-linked aromatic polyimide polymer membrane described in the present invention may incorporate a species that adsorbs strongly to certain gases (e.g. cobalt porphyrins or phthalocyanines for $O_2$ or silver (I) for ethane) to facilitate their transport across the membrane.

The PBO membrane made from the self-cross-linked aromatic polyimide polymer membrane described in the present invention also has immediate application to concentrate olefin in a paraffin/olefin stream for olefin cracking application. For example, the PBO membrane made from the self-cross-linked aromatic polyimide polymer membrane described in the present invention can be used for propylene/propane separation to increase the concentration of the effluent in a catalytic dehydrogenation reaction for the production of propylene from propane and isobutylene from isobutane. Therefore, the number of stages of a propylene/propane splitter that is required to get polymer grade propylene can be reduced. Another application for the PBO membrane made from the self-cross-linked aromatic polyimide polymer membrane described in the present invention is for separating isoparaffin and normal paraffin in light paraffin isomerization and MaxEne™, a process for enhancing the concentration of normal paraffin (n-paraffin) in the naphtha cracker feedstock, which can be then converted to ethylene.

The PBO membrane made from the self-cross-linked aromatic polyimide polymer membrane described in the present invention can also be operated at high temperature to provide the sufficient dew point margin for natural gas upgrading (e.g., $CO_2$ removal from natural gas). The PBO membrane made from the self-cross-linked aromatic polyimide polymer membrane described in the present invention can be used in either a single stage membrane or as the first or/and second stage membrane in a two stage membrane system for natural gas upgrading.

The PBO membrane made from the self-cross-linked aromatic polyimide polymer membrane described in the present invention may also be used in the separation of liquid mixtures by pervaporation, such as in the removal of organic compounds (e.g., alcohols, phenols, chlorinated hydrocarbons, pyridines, ketones) from water such as aqueous effluents or process fluids. A membrane which is ethanol-selective would be used to increase the ethanol concentration in relatively dilute ethanol solutions (5-10% ethanol) obtained by fermentation processes. Another liquid phase separation example using the PBO membrane made from the self-cross-linked aromatic polyimide polymer membrane described in the present invention is the deep desulfurization of gasoline and diesel fuels by a pervaporation membrane process similar to the process described in U.S. Pat. No. 7,048,846, incorporated by reference herein in its entirety. The PBO membrane made from the self-cross-linked aromatic polyimide polymer membrane described in the present invention that are selective to sulfur-containing molecules would be used to selectively remove sulfur-containing molecules from fluid catalytic cracking (FCC) and other naphtha hydrocarbon streams. Further liquid phase examples include the separation of one organic component from another organic component, e.g. to separate isomers of organic compounds. Mixtures of organic compounds which may be separated using the PBO membrane made from the self-cross-linked aromatic polyimide polymer membrane described in the present invention include: ethylacetate-ethanol, diethylether-ethanol, acetic acid-ethanol, benzene-ethanol, chloroform-ethanol, chloroform-methanol, acetone-isopropylether, allylalcohol-allylether, allylalcohol-cyclohexane, butanol-butylacetate, butanol-1-butylether, ethanol-ethylbutylether, propylacetate-propanol, isopropylether-isopropanol, methanol-ethanol-isopropanol, and ethylacetate-ethanol-acetic acid.

EXAMPLES

The following examples are provided to illustrate one or more preferred embodiments of the invention, but are not limited embodiments thereof. Numerous variations can be made to the following examples that lie within the scope of the invention.

Example 1

Synthesis of Self-Cross-Linkable Aromatic Polyimide poly[2,2'-bis-(3,4-dicarboxyphenyl)hexafluoropropane dianhydride-3,5-diaminobenzoic acid-3,3'-dihydroxy-4,4'-diamino-biphenyl] (Abbreviated as poly(6FDA-HAB-DBA))

Poly(6FDA-HAB-DBA) polyimide was synthesized from polycondensation reaction of 2,2'-bis-(3,4-dicarboxyphenyl) hexafluoropropane dianhydride (6FDA) with a mixture of 3,5-diaminobenzoic acid (DBA) and 3,3'-dihydroxy-4,4'-diamino-biphenyl (HAB) in DMAc polar solvent by a two-step process involving the formation of the poly(amic acid) followed by a solution imidization process. Acetic anhydride was used as the dehydrating agent and pyridine was used as the imidization catalyst for the solution imidization reaction. For example, a 1 L three-neck round-bottom flask equipped with a nitrogen inlet and a mechanical stirrer was charged with 25.9 g (0.12 mol) of HAB, 4.56 g (0.03 mol) of DBA and 121.8 g of DMAc. Once HAB and DBA were fully dissolved, 66.6 g of 6FDA (0.15 mol) was added to the HAB and DBA solution in the flask. Then 428 g of DMAc was added to the solution. The reaction mixture was mechanically stirred for 24 hours at ambient temperature to give a viscous poly(amic acid) solution. Then 32.1 g (0.315 mol) of acetic anhydride and 49.8 g (0.63 mol) of pyridine were added to the reaction mixture under stirring. The reaction mixture was mechanically stirred for an additional 3 hour at 95° C. to yield the poly(6FDA-HAB-DBA) polyimide. The poly(6FDA-HAB-DBA) polyimide product in a power form was recovered by adding methanol to the reaction mixture under mechanical stirring. The resultant poly(6FDA-HAB-DBA) polyimide powder was then thoroughly rinsed with methanol and dried in a vacuum oven at 110° C. for 24 hours.

Example 2

Preparation and Evaluation of PBO Membrane from Self-Cross-Linked Aromatic Polyimide Membrane 5.0 g of self-cross-linkable poly(6FDA-HAB-DBA) polyimide synthesized in Example 1 was dissolved in 20.0 g of NMP solvent. The mixture was mechanically stirred for 2 hours to form a homogeneous casting dope. The resulting homogeneous casting dope was allowed to degas overnight. The self-cross-linkable poly(6FDA-HAB-DBA) membrane was prepared from the bubble free casting dope on a clean glass plate using a doctor knife with a 15-mil gap. The membrane together with the glass plate was then put into a vacuum oven. The solvents were removed by slowly increasing the vacuum and the temperature of the vacuum oven. Finally, the membrane was heated at 200° C. under vacuum for 48 hours to completely remove the residual solvents. The dried self-cross-linkable poly(6FDA-HAB-DBA) membrane was heated at 300° C. under $N_2$ for 10 min to form the self-cross-linked poly(6FDA-HAB-DBA) membrane via esterification reaction between the carboxylic acid groups and the hydroxyl groups on poly(6FDA-HAB-DBA) polymer chains. The self-cross-linked poly(6FDA-HAB-DBA) aromatic polyimide membrane became insoluble in organic solvents.

The self-cross-linked poly(6FDA-HAB-DBA) membrane was then thermally rearranged by heating from 60° to 450° C. at a heating rate of 15° C./min in a regular tube furnace under $N_2$ flow. The membrane was held for 10 min at 450° C. and then cooled down to 50° C. at a cooling rate of 15° C./min under $N_2$ flow to yield PBO(6FDA-HAB-DBA) membrane.

The PBO(6FDA-HAB-DBA) membrane made from the self-cross-linked poly(6FDA-HAB-DBA) aromatic polyimide membrane is useful for a variety of gas separation applications such as $CO_2/CH_4$, $H_2/CH_4$, and $He/CH_4$ separations. The membrane was tested for $CO_2/CH_4$ and $H_2/CH_4$ separations at 50° C. under 791 kPa (100 psig) pure single feed gas pressure. The results show that the self-cross-linked poly (6FDA-HAB-DBA) aromatic polyimide membrane has $CO_2$ permeance of 7.77 Barrers and $CO_2/CH_4$ selectivity of 52.5 for $CO_2/CH_4$ separation. The PBO(6FDA-HAB-DBA) membrane made from the self-cross-linked poly(6FDA-HAB-DBA) aromatic polyimide membrane showed significantly improved $CO_2$ permeance compared to the self-cross-linked poly(6FDA-HAB-DBA) aromatic polyimide membrane for $CO_2/CH_4$ separation (Table 1). The PBO(6FDA-HAB-DBA) membrane made from the self-cross-linked poly(6FDA-HAB-DBA) aromatic polyimide membrane also showed significantly improved $H_2$ permeance compared to the self-cross-linked poly(6FDA-HAB-DBA) aromatic polyimide membrane for $H_2/CH_4$ separation (Table 2).

TABLE 1

Pure gas permeation test results of self-cross-linkable poly(6FDA-HAB-DBA) membrane, self-cross-linked poly(6FDA-HAB-DBA) membrane, and PBO(6FDA-HAB-DBA) membrane for $CO_2/CH_4$ Separation[a]

| Membrane | $P_{CO2}$ (Barrer) | $\alpha_{CO2/CH4}$ |
|---|---|---|
| Self-cross-linkable poly(6FDA-HAB-DBA) | 5.13 | 49.3 |
| Self-cross-linked poly(6FDA-HAB-DBA) | 7.77 | 52.5 |
| PBO(6FDA-HAB-DBA) | 209.9 | 25.9 |

[a]$P_{CO2}$ and $P_{CH4}$ were tested at 50° C. and 690 kPa (100 psig);
1 Barrer = $10^{-10}$ cm$^3$ (STP) · cm/cm$^2$ · sec · cmHg.

TABLE 2

Pure gas permeation test results of self-cross-linkable poly(6FDA-HAB-DBA) membrane, self-cross-linked poly(6FDA-HAB-DBA) membrane, and PBO(6FDA-HAB-DBA) membrane for $H_2/CH_4$ Separation[a]

| Membrane | $P_{H2}$ (Barrer) | $\alpha_{H2/CH4}$ |
|---|---|---|
| Self-cross-linkable poly(6FDA-HAB-DBA) | 22.9 | 220.1 |
| Self-cross-linked poly(6FDA-HAB-DBA) | 38.5 | 260.3 |
| PBO(6FDA-HAB-DBA) | 337.1 | 41.5 |

[a]$P_{H2}$ and $P_{CH4}$ were tested at 50° C. and 690 kPa (100 psig);
Barrer = $10^{-10}$ cm$^3$ (STP) · cm/cm$^2$ · sec · cmHg An embodiment of the invention involves a method of making a polybenzoxazole membrane comprising (a) fabricating a self-cross-linkable aromatic polyimide polymer membrane from the self-cross-linkable aromatic polyimide polymer comprising both hydroxyl functional groups and carboxylic acid functional groups; (b) cross-linking the self-cross-linkable aromatic polyimide polymer membrane to form a self-cross-linked aromatic polyimide polymer membrane by heating the membrane at 250° C. to 300° C. under an inert atmosphere; and (c) thermal heating the self-cross-linked aromatic polyimide polymer membrane at a temperature from about 350° to 500° C. under an inert atmosphere, such as argon, nitrogen, or vacuum to convert the self-cross-linked aromatic polyimide polymer membrane into a polybenzoxazole membrane.

The self-cross-linkable aromatic polyimide polymer used for the preparation of PBO membrane described in the present invention comprise a formula (I):

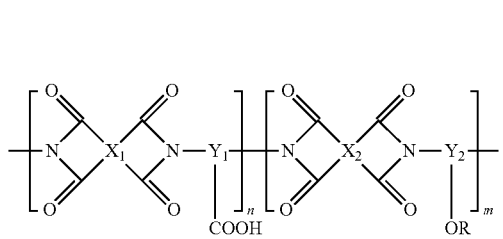

wherein $X_1$ and $X_2$ are selected from the group consisting of

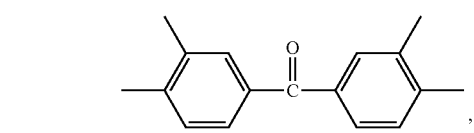

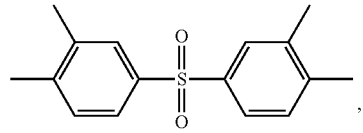

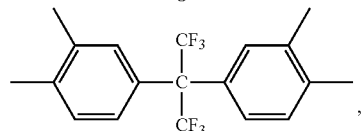

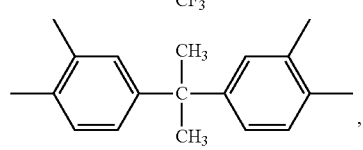

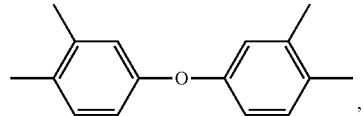

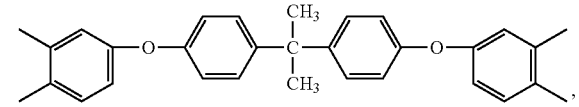

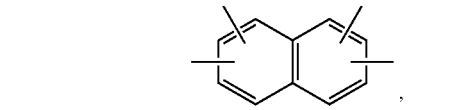

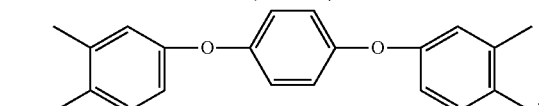

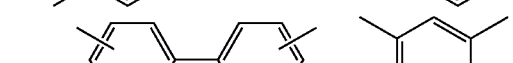

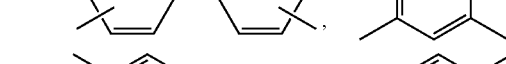

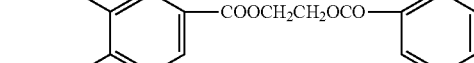

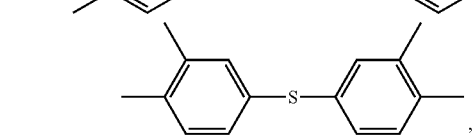

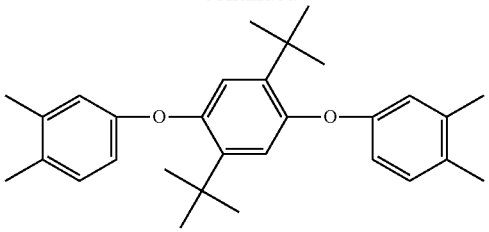

and mixtures thereof, respectively; $X_1$ and $X_2$ are the same or different from each other; $Y_1$—COOH is selected from the group consisting of

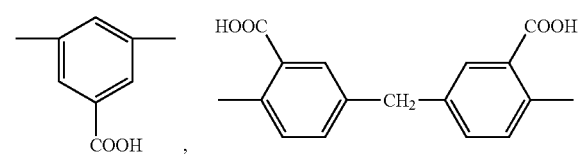

and mixtures thereof; $Y_2$—OR is selected from the group consisting of

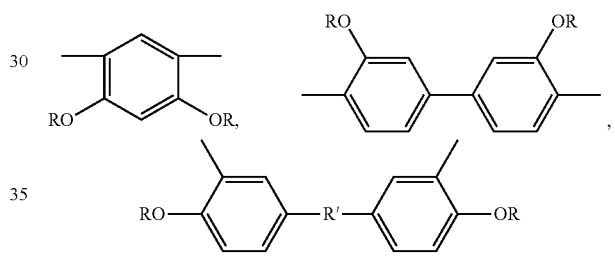

and mixtures thereof, and —R— is selected from the group consisting of —H and a mixture of —H and —$COCH_3$, and —R'— is selected from the group consisting of

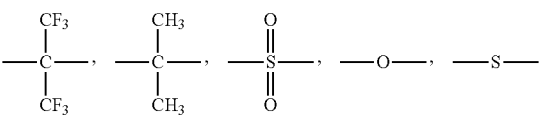

and mixtures thereof; n and m are independent integers from 2 to 500; the molar ratio of n/m is in a range of 1:1 to 1:20.

In the self-cross-linkable aromatic polyimide polymer in formula (I), $X_1$ and $X_2$ may be selected from the group consisting of

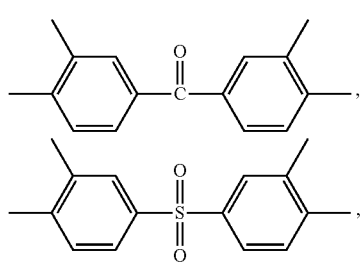

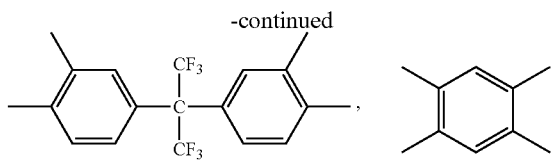

and mixtures thereof. In the process of the invention, in formula (I) $Y_1$—COOH may be

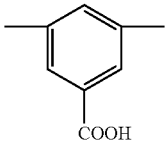

In the process of the invention, the self-cross-linkable aromatic polyimide polymer in formula (I) may include $Y_2$—OR that is selected from the group consisting of

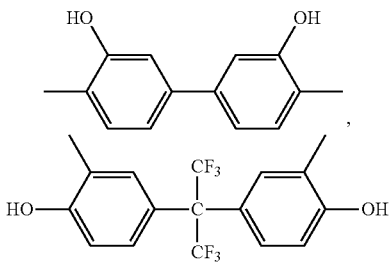

and mixtures thereof.

In an embodiment of the invention, the self-cross-linkable aromatic polyimide polymer comprising both hydroxyl functional groups and carboxylic acid functional groups are selected from the group consisting of poly(3,3',4,4'-diphenylsulfone tetracarboxylic dianhydride-3,5-diaminobenzoic acid-3,3'-dihydroxy-4,4'-diamino-biphenyl)polyimide derived from a polycondensation reaction of 3,3',4,4'-diphenylsulfone tetracarboxylic dianhydride with a mixture of 3,5-diaminobenzoic acid and 3,3'-dihydroxy-4,4'-diamino-biphenyl; poly(3,3',4,4'-benzophenone tetracarboxylic dianhydride-pyromellitic dianhydride-3,5-diaminobenzoic acid-3,3'-dihydroxy-4,4'-diamino-biphenyl)polyimide derived from a polycondensation reaction of 3,3',4,4'-benzophenone tetracarboxylic dianhydride and pyromellitic dianhydride with 3,5-diaminobenzoic acid and 3,3'-dihydroxy-4,4'-diamino-biphenyl; poly(3,3',4,4'-benzophenone tetracarboxylic dianhydride-3,5-diaminobenzoic acid-3,3'-dihydroxy-4,4'-diamino-biphenyl)polyimide derived from a polycondensation reaction of 3,3',4,4'-benzophenone tetracarboxylic dianhydride with 3,5-diaminobenzoic acid and 3,3'-dihydroxy-4,4'-diamino-biphenyl; poly[2,2'-bis-(3,4-dicarboxyphenyl)hexafluoropropane dianhydride-3,5-diaminobenzoic acid-3,3'-dihydroxy-4,4'-diamino-biphenyl]polyimide derived from the polycondensation reaction of 2,2'-bis-(3,4-dicarboxyphenyl)hexafluoropropane dianhydride with a mixture of 3,5-diaminobenzoic acid and 3,3'-dihydroxy-4,4'-diamino-biphenyl; poly[2,2'-bis-(3,4-dicarboxyphenyl) hexafluoropropane dianhydride-2,2-bis(3-amino-4-hydroxyphenyl)-hexafluoropropane-3,5-diaminobenzoic acid] derived from a polycondensation reaction of 2,2'-bis-(3,4-dicarboxyphenyl)hexafluoropropane dianhydride with a mixture of 2,2-bis(3-amino-4-hydroxyphenyl)-hexafluoropropane and 3,5-diaminobenzoic acid; poly[3,3',4,4'-benzophenonetetracarboxylic dianhydride-2,2-bis(3-amino-4-hydroxyphenyl)-hexafluoropropane-3,5-diaminobenzoic acid] derived from a polycondensation reaction of 3,3',4,4'-benzophenonetetracarboxylic dianhydride with a mixture of 2,2-bis(3-amino-4-hydroxyphenyl)-hexafluoropropane and 3,5-diaminobenzoic acid; poly[4,4'-oxydiphthalic anhydride-2,2-bis(3-amino-4-hydroxyphenyl)-hexafluoropropane-3,5-diaminobenzoic acid] derived from a polycondensation reaction of 4,4'-oxydiphthalic anhydride with a mixture of 2,2-bis(3-amino-4-hydroxyphenyl)-hexafluoropropane and 3,5-diaminobenzoic acid; poly[3,3',4,4'-diphenylsulfone tetracarboxylic dianhydride-2,2-bis(3-amino-4-hydroxyphenyl)-hexafluoropropane-3,5-diaminobenzoic acid] derived from a polycondensation reaction of 3,3',4,4'-diphenylsulfone tetracarboxylic dianhydride with a mixture of 2,2-bis(3-amino-4-hydroxyphenyl)-hexafluoropropane and 3,5-diaminobenzoic acid; poly[2,2'-bis-(3,4-dicarboxyphenyl)hexafluoropropane dianhydride-3,3',4,4'-benzophenonetetracarboxylic dianhydride-2,2-bis(3-amino-4-hydroxyphenyl)-hexafluoropropane-3,5-diaminobenzoic acid] derived from a polycondensation reaction of 2,2'-bis-(3,4-dicarboxyphenyl)hexafluoropropane dianhydride and 3,3',4,4'-benzophenonetetracarboxylic dianhydride with a mixture of 2,2-bis(3-amino-4-hydroxyphenyl)-hexafluoropropane and 3,5-diaminobenzoic acid; poly[4,4'-oxydiphthalic anhydride-2,2-bis(3-amino-4-hydroxyphenyl)-hexafluoropropane-3,3'-dihydroxy-4,4'-diamino-biphenyl-3,5-diaminobenzoic acid] derived from a polycondensation reaction of 4,4'-oxydiphthalic anhydride with a mixture of 2,2-bis(3-amino-4-hydroxyphenyl)-hexafluoropropane, 3,3'-dihydroxy-4,4'-diamino-biphenyl and 3,5-diaminobenzoic acid; poly[3,3',4,4'-benzophenonetetracarboxylic dianhydride-2,2-bis(3-amino-4-hydroxyphenyl)-hexafluoropropane-3,3'-dihydroxy-4,4'-diamino-biphenyl-3,5-diaminobenzoic acid] derived from a polycondensation reaction of 3,3',4,4'-benzophenonetetracarboxylic dianhydride with a mixture of 2,2-bis(3-amino-4-hydroxyphenyl)-hexafluoropropane, 3,3'-dihydroxy-4,4'-diamino-biphenyl, and 3,5-diaminobenzoic acid.

In another embodiment of the invention, the self-cross-linkable aromatic polyimide polymer comprising both hydroxyl functional groups and carboxylic acid functional groups is selected from the group consisting of poly(3,3',4,4'-diphenylsulfone tetracarboxylic dianhydride-3,5-diaminobenzoic acid-3,3'-dihydroxy-4,4'-diamino-biphenyl)polyimide derived from a polycondensation reaction of 3,3',4,4'-diphenylsulfone tetracarboxylic dianhydride with a mixture of 3,5-diaminobenzoic acid and 3,3'-dihydroxy-4,4'-diamino-biphenyl; poly(3,3',4,4'-benzophenone tetracarboxylic dianhydride-pyromellitic dianhydride-3,5-diaminobenzoic acid-3,3'-dihydroxy-4,4'-diamino-biphenyl)polyimide derived from a polycondensation reaction of 3,3',4,4'-benzophenone tetracarboxylic dianhydride and pyromellitic dianhydride with 3,5-diaminobenzoic acid and 3,3'-dihydroxy-4,4'-diamino-biphenyl; poly[2,2'-bis-(3,4-dicarboxyphenyl)hexafluoropropane dianhydride-3,5-diaminobenzoic acid-3,3'-dihydroxy-4,4'-diamino-biphenyl]polyimide derived from the polycondensation reaction of 2,2'-bis-(3,4-dicarboxyphenyl)hexafluoropropane dianhydride with a mixture of 3,5-diaminobenzoic acid and 3,3'-dihydroxy-4,4'-diamino-biphenyl; poly[3,3',4,4'-diphenylsulfone tetracarboxylic dianhydride-2,2-bis(3-amino-4-hydroxyphenyl)-hexafluoropropane-3,5-diaminobenzoic acid] derived from a polycondensation reaction of 3,3',4,4'-diphenylsulfone tetracarboxylic dianhydride with a mixture of 2,2-bis(3- amino-4-hydroxyphenyl)-hexafluoropropane and 3,5-diaminobenzoic acid; poly[3,3',4,4'-benzophenonetetracarboxylic dianhydride-2,2-bis(3-amino-4-hydroxyphenyl)-hexafluoropropane-3,3'-dihydroxy-4,4'-diamino-biphenyl-3,5-diaminobenzoic acid] derived from a polycondensation reaction of 3,3',4,4'-benzophenonetetracarboxylic dianhydride with a mixture of 2,2-bis(3-amino-4-hydroxyphenyl)-hexafluoropropane, 3,3'-dihydroxy-4,4'-diamino-biphenyl, and 3,5-diaminobenzoic acid.

In another embodiment of the invention, the self-cross-linked aromatic polyimide polymer form from the self-cross-linkable aromatic polyimide polymer described comprises a plurality of repeating units of formula (II):

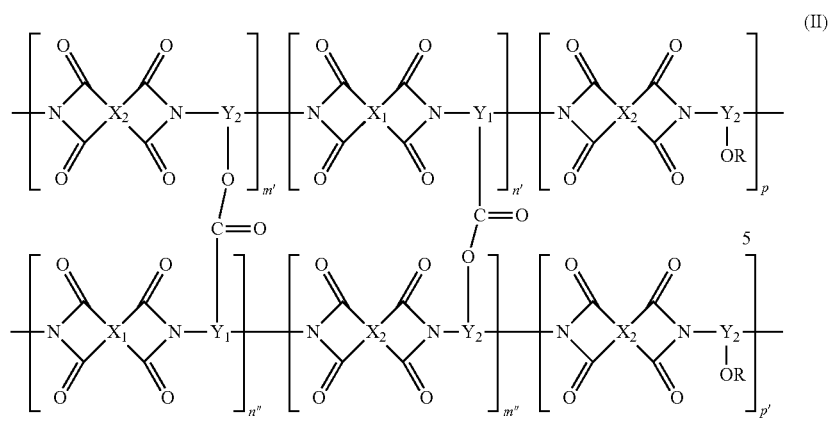

wherein $X_1$ and $X_2$ are selected from the group consisting of

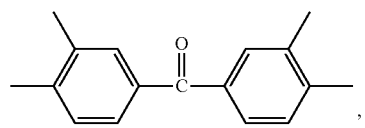

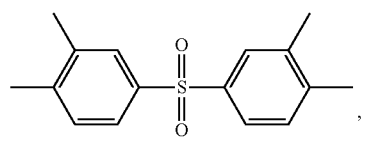

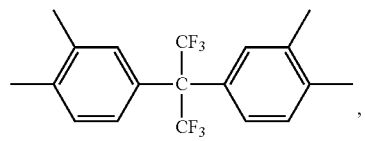

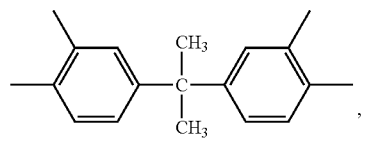

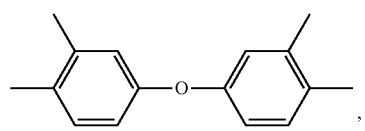

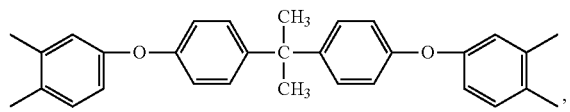

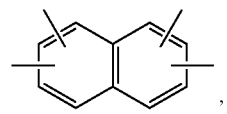

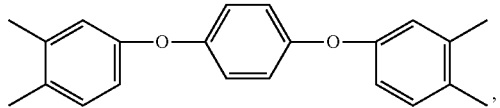

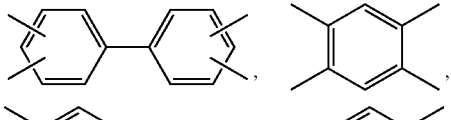

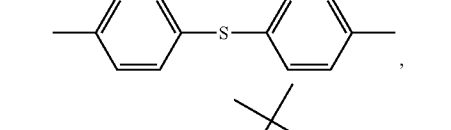

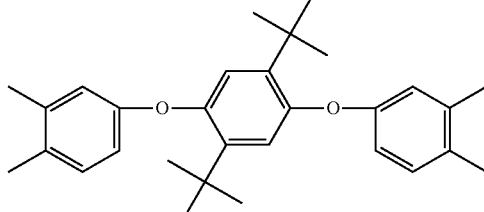

and mixtures thereof, respectively; $X_1$ and $X_2$ are the same or different from each other; $Y_1$—CO— is selected from the group consisting of

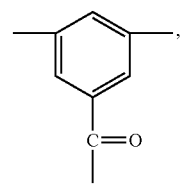

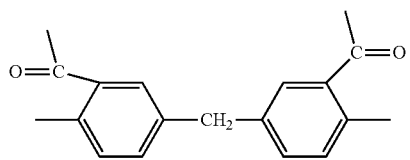

and mixtures thereof; Y$_2$—O— is selected from the group consisting of

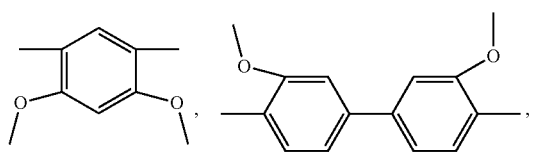

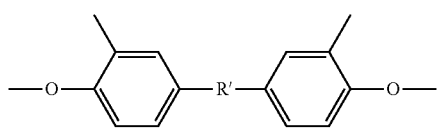

and mixtures thereof, and —R'— is selected from the group consisting of

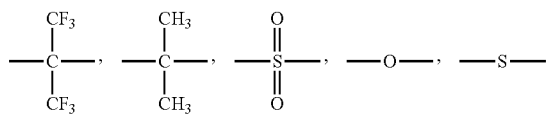

and mixtures thereof; Y$_2$—OR is selected from the group consisting of

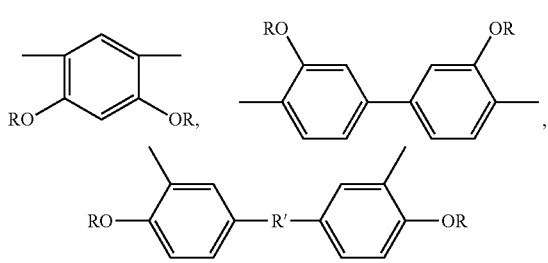

and mixtures thereof, and —R— is selected from the group consisting of —H and a mixture of —H and —COCH$_3$, and —R'— is selected from the group consisting of

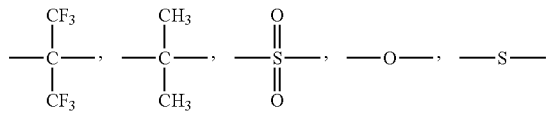

and mixtures thereof; n', n", m', m", p, and p' are independent integers from 2 to 500; the molar ratio of n'/(m'+p) is in a range of 1:1 to 1:20; the molar ratio of n"/(m"+p') is in a range of 1:1 to 1:20. In embodiments of the invention in formula (II), Y$_1$—CO— may be

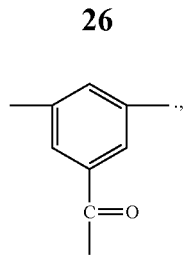

Y$_2$—O— may be selected from the group consisting of

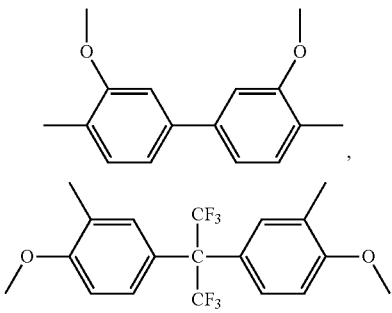

and mixtures thereof, and Y$_2$—OR may be selected from the group consisting of

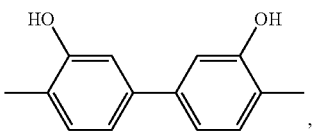

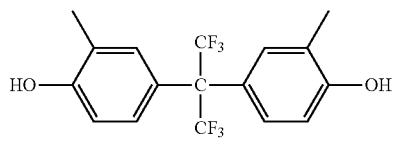

and mixtures thereof. In an embodiment of the invention, the polybenzoxazole polymer comprises repeating units of a formula (III), wherein said formula (III) is:

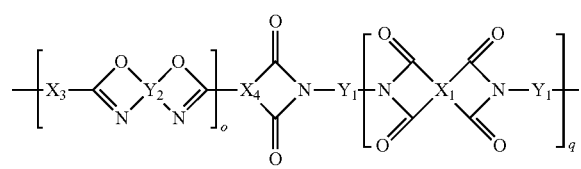

wherein X$_1$ is selected from the group consisting of

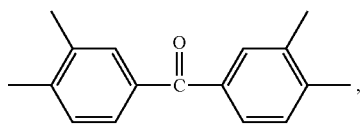

-continued
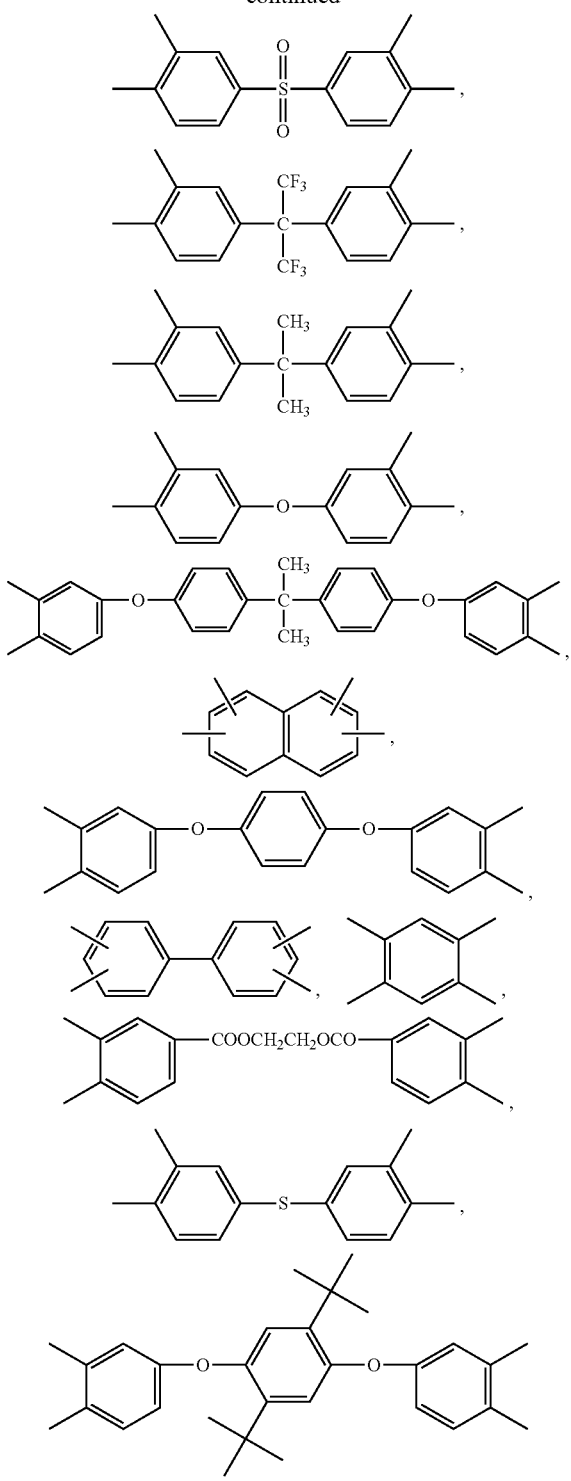
and mixtures thereof; wherein $X_3$ is selected from the group consisting of
-continued
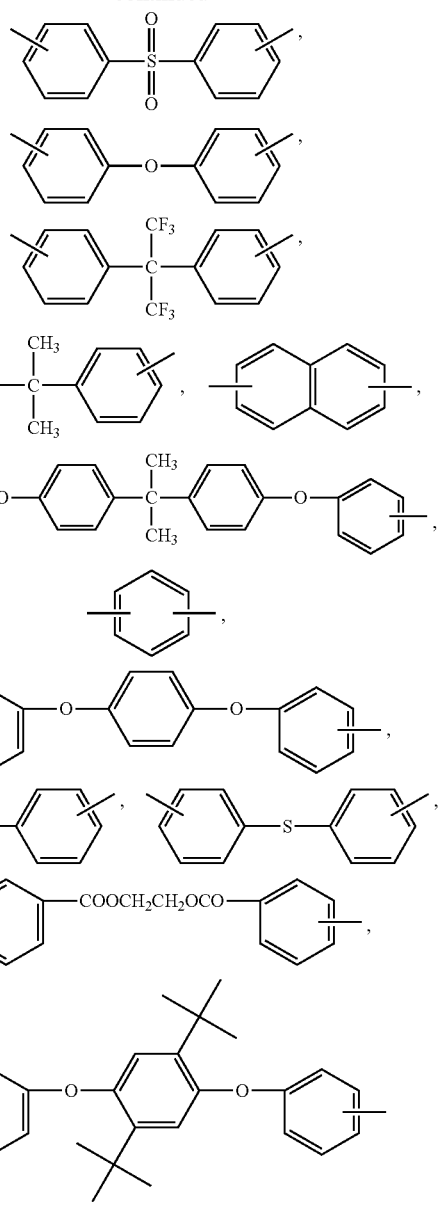
and mixtures thereof; wherein $X_4$ is selected from the group consisting of
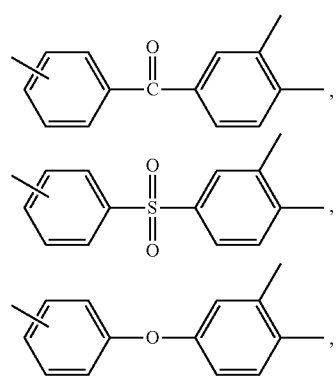

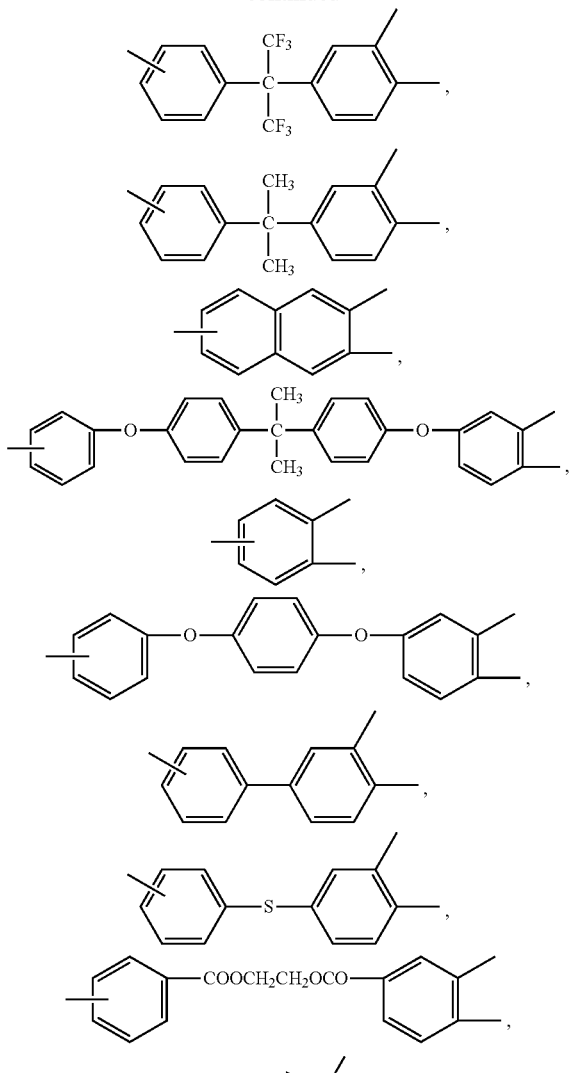

and mixtures thereof; $Y_1$ is selected from the group consisting of

and mixtures thereof; $Y_2$ is selected from the group consisting of

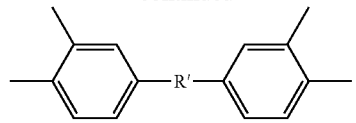

and mixtures thereof, and —R'— is selected from the group consisting of

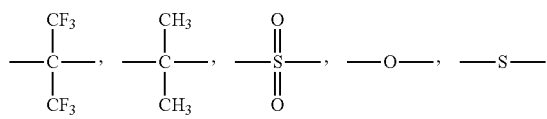

and mixtures thereof; o and q are independent integers from 2 to 500. In an embodiment of the invention, $X_1$ may be selected from the group consisting of

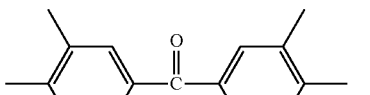

and mixtures thereof; X3 may be selected from the group consisting of

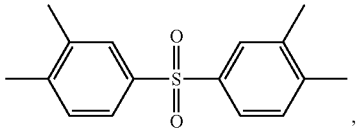

$X_4$ may be selected from the group consisting of

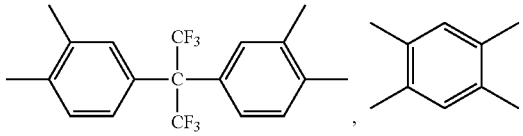

-continued

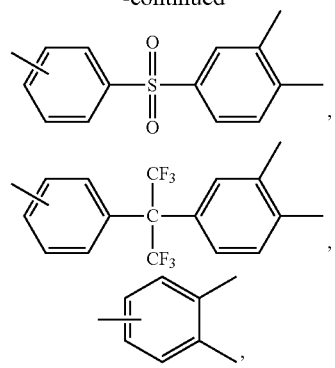

Y₁ may be

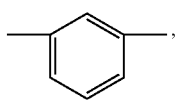

and
Y₂ may be selected from the group consisting of

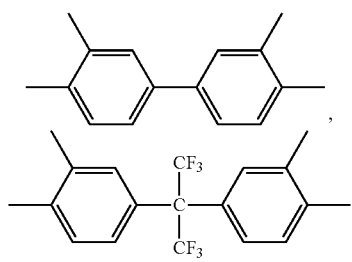

and mixtures thereof.

The method of preparing the membranes of the invention may further comprise application of a high permeability material to a surface of said polybenzoxazole membrane wherein said high permeability material is selected from the group consisting of a polysiloxane, a fluoro-polymer, a thermally curable silicone rubber, or a UV radiation curable epoxy silica. The polybenzoxazole membrane may be fabricated into a flat sheet, tube or hollow fiber membrane or other form as known to one of skill in the art.

The invention also involves preparation of a polybenzoxazole membrane prepared by any of the preceding embodiments.

In another embodiment of the invention is provided a process for separating at least one gas from a mixture of gases comprising providing a self-cross-linked aromatic polyimide membrane of formula (III) comprising wherein said formula (III) is:

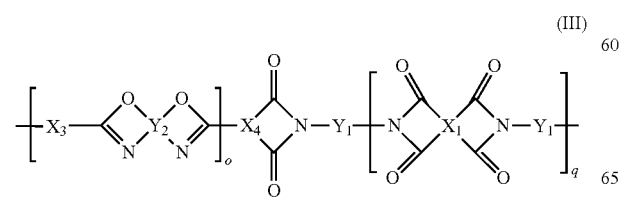

(III)

wherein $X_1$ is selected from the group consisting of

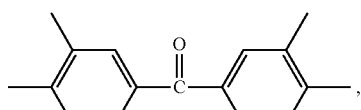

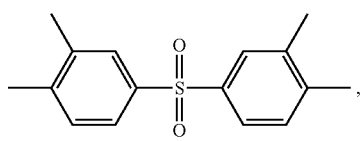

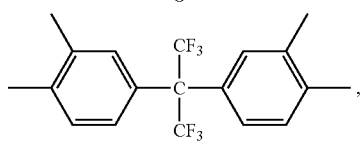

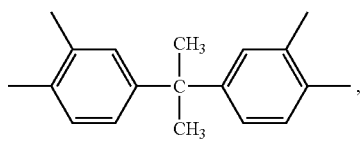

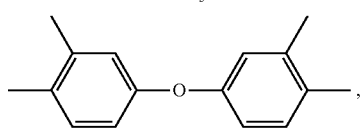

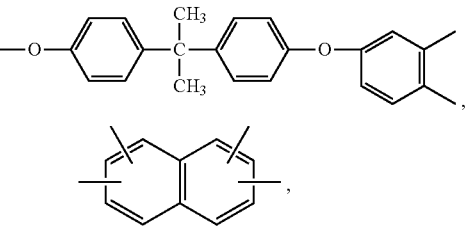

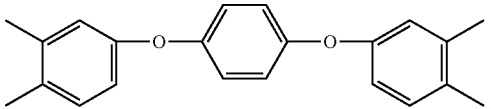

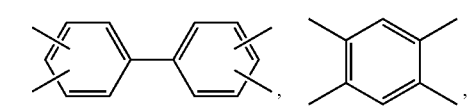

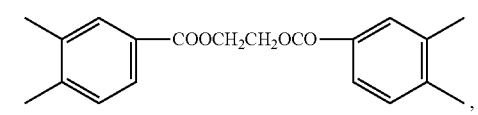

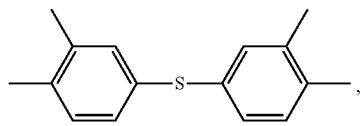

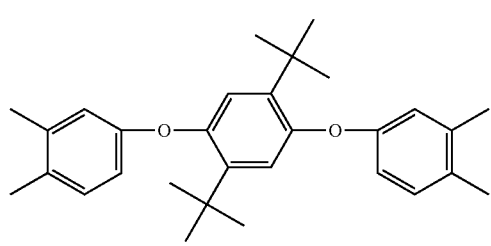

and mixtures thereof; wherein $X_3$ is selected from the group consisting of
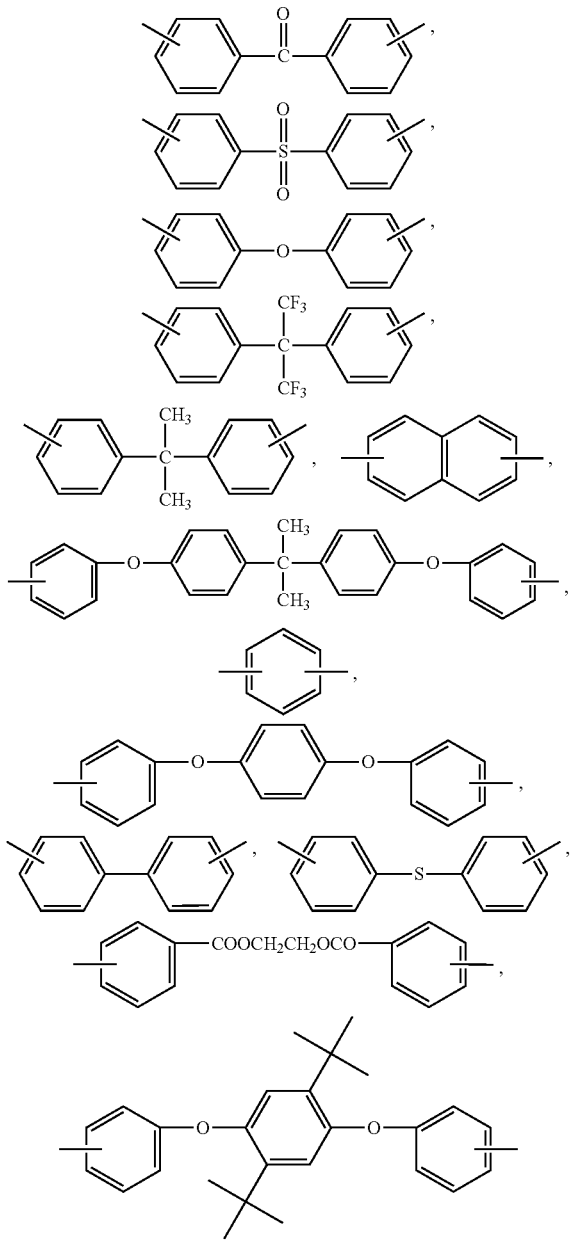
and mixtures thereof; wherein $X_4$ is selected from the group consisting of
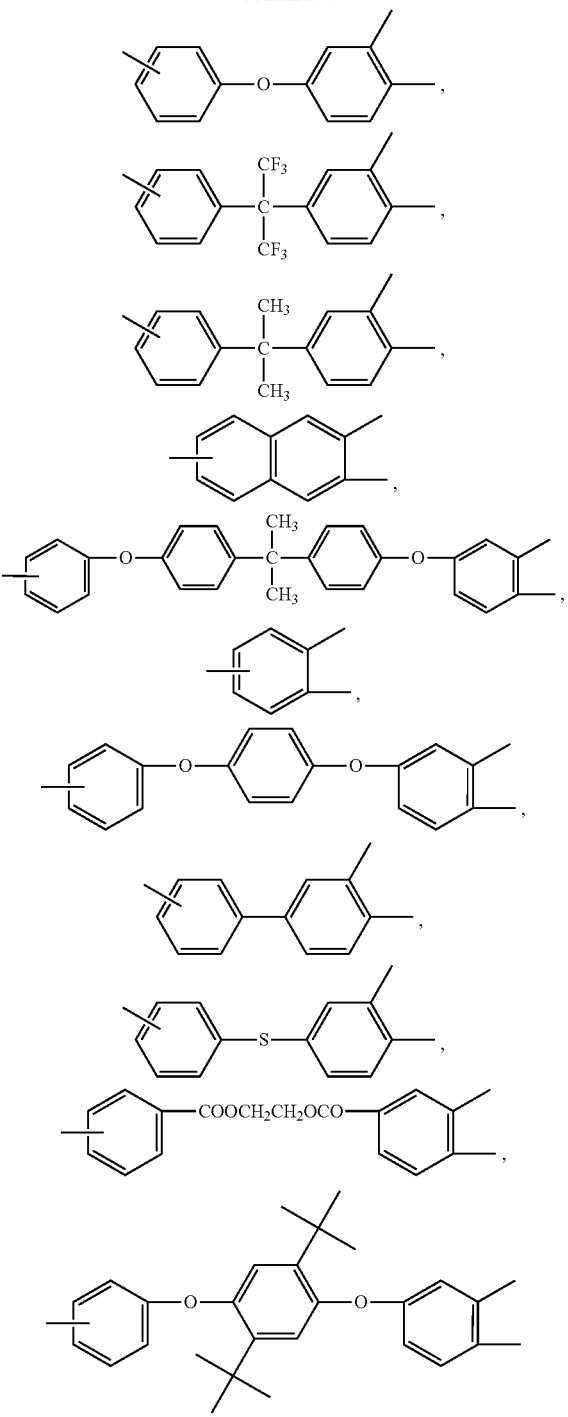
and mixtures thereof; $Y_1$ is selected from the group consisting of
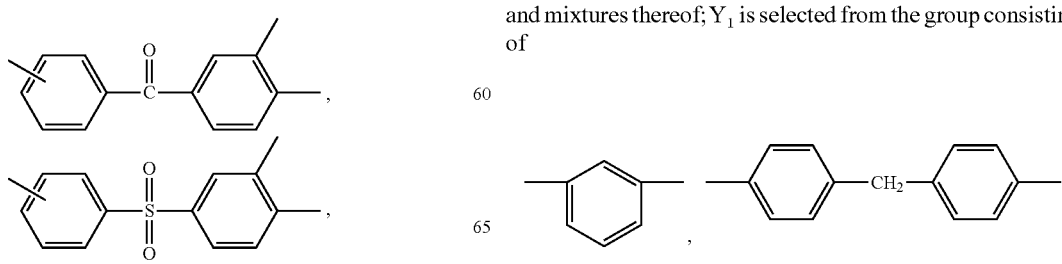

and mixtures thereof; $Y_2$ is selected from the group consisting of

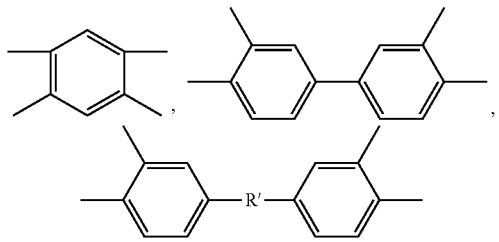

and mixtures thereof, and —R'— is selected from the group consisting of

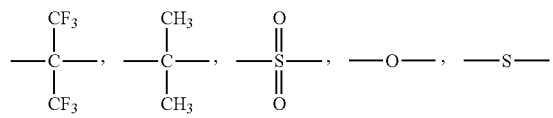

and mixtures thereof; o and q are independent integers from 2 to 500 contacting the mixture of gases to one side of the polybenzoxazole membrane of formula (III) to cause at least one gas to permeate said membrane; and removing from an opposite side of the polybenzoxazole membrane of formula (III) a permeate gas composition comprising a portion of said at least one gas that permeated said membrane. In formula (III), $X_1$ may be selected from the group consisting of

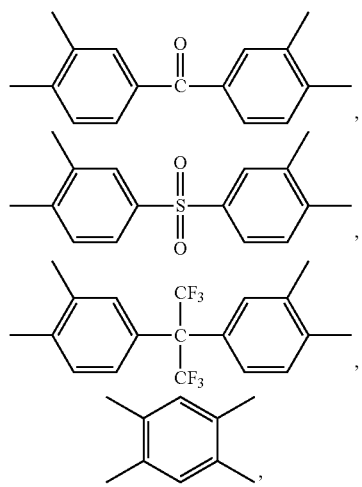

and mixtures thereof, X3 may be selected from the group consisting of

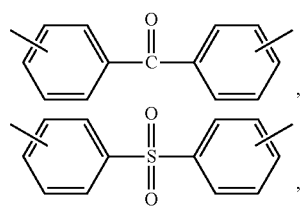

-continued

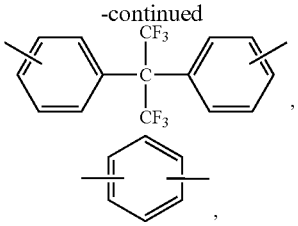

$X_4$ may be selected from the group consisting of

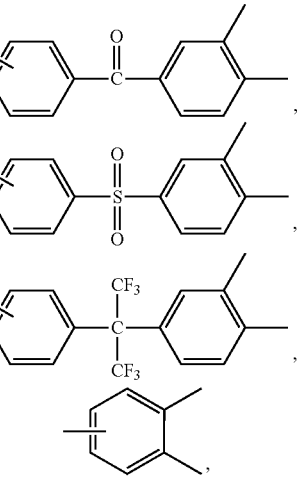

$Y_1$ may be

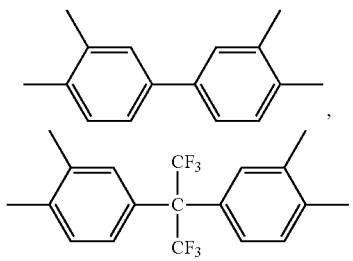

and
$Y_2$ may be selected from the group consisting of and mixtures thereof.

The mixture of gases may be any mixture of gases that may be separated by a membrane. The mixture of gases may be a mixture of carbon dioxide and methane, a mixture of hydrogen and methane, or a mixture of helium and methane as well as other gases found in natural gas. The mixture of gases may comprise a mixture of at least one volatile organic compound and at least one atmospheric gas. The mixture of gases may comprise nitrogen and hydrogen. The mixture of gases treated by the membranes of this invention may comprise a mixture of carbon dioxide, oxygen, nitrogen, water vapor, hydrogen sulfide, helium and methane.

In some embodiments of the invention, the membrane may comprise a species that adsorbs strongly to at least one gas. In some embodiments of the invention, the mixture of gases comprises a mixture of paraffins and olefins.

Another embodiment of the invention involves a process for separation of liquid mixtures by pervaporation comprising contacting said liquid mixture with a polybenzoxazole membrane of formula (III) comprising wherein said formula (III) is:

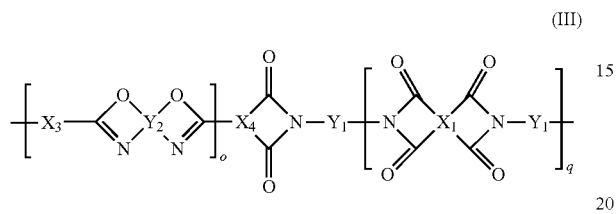

(III)

wherein $X_1$ is selected from the group consisting of and mixtures thereof; wherein $X_3$ is selected from the group consisting of

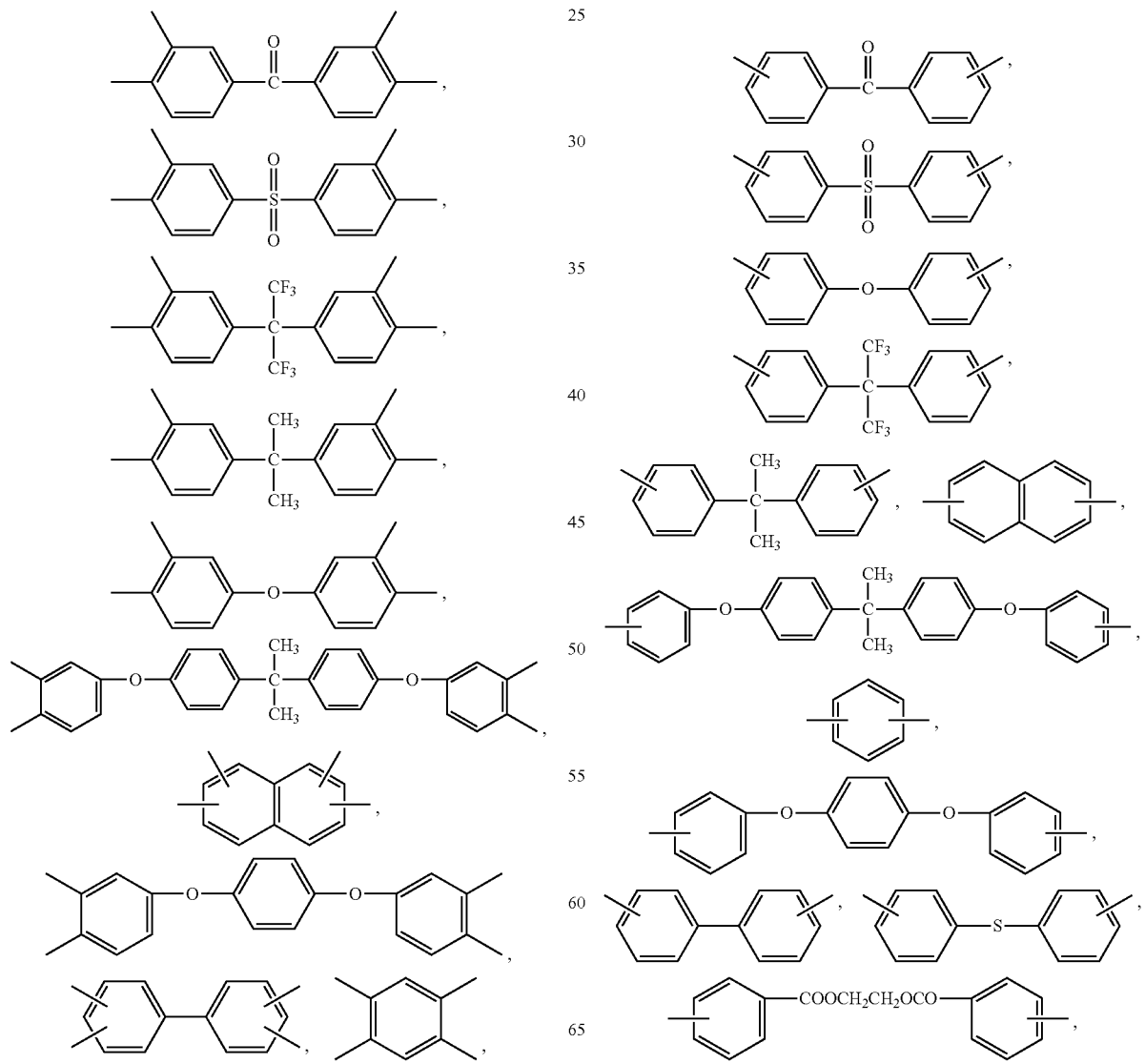

-continued

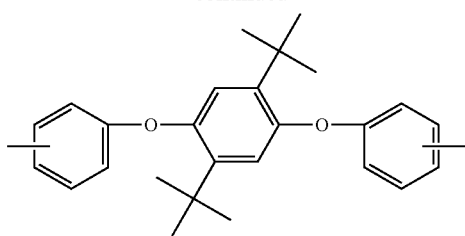

and mixtures thereof; wherein $X_4$ is selected from the group consisting of

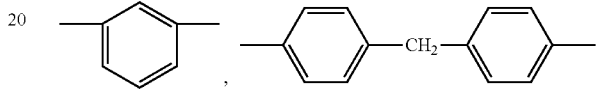

-continued

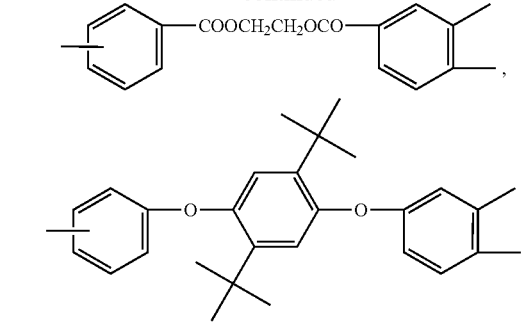

and mixtures thereof; $Y_1$ is selected from the group consisting of

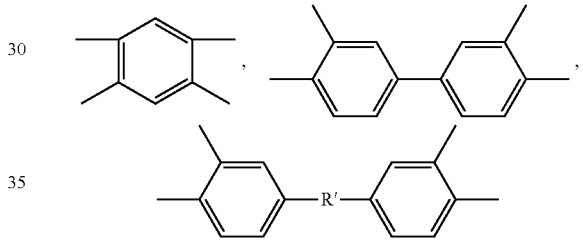

and mixtures thereof; $Y_2$ is selected from the group consisting of and mixtures thereof, and —R'— is selected from the group consisting of

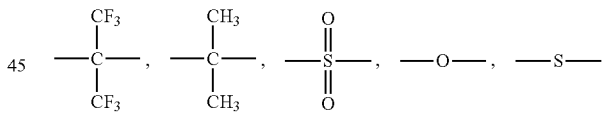

and mixtures thereof; o and q are independent integers from 2 to 500 contacting the mixture of liquids to one side of the polybenzoxazole membrane of formula (III) to cause at least one gas to permeate said membrane; and removing from an opposite side of said polybenzoxazole membrane of formula (III) a permeate liquid composition comprising a portion of said at least one liquid that permeated said membrane.

The liquid mixture may comprise water and one or more organic compounds selected from the group consisting of alcohols, phenols, chlorinated hydrocarbons, pyridines, and ketones and the process involves separation of water from the one or more organic compounds. The liquid mixture may comprise sulfur-containing molecules in a hydrocarbon stream such as naphtha. The membranes used in the process can be used to remove such sulfur-containing molecules from diesel or gasoline products. In another embodiment of the invention, the liquid mixture may comprise a mixture of isomers of organic compounds. The liquid mixture may comprise a mixture selected from the group consisting of: ethylacetate-ethanol, diethylether-ethanol, acetic acid-ethanol, benzene-ethanol, chloroform-ethanol, chloroform-methanol, acetone-isopropylether, allylalcohol-allylether, allylalcohol-cyclohexane, butanol-butylacetate, butanol-1-butylether, ethanol-ethylbutylether, propylacetate-propanol, isopropylether-isopropanol, methanol-ethanol-isopropanol, and ethylacetate-ethanol-acetic acid.

In another embodiment of the invention, the liquid mixture comprises a dilute ethanol solution and where said process increases an ethanol concentration in said liquid mixture.

The invention claimed is:
1. A process for separating at least one gas from a mixture of gases comprising providing a polybenzoxazole membrane of formula (III) wherein said formula (III) is:

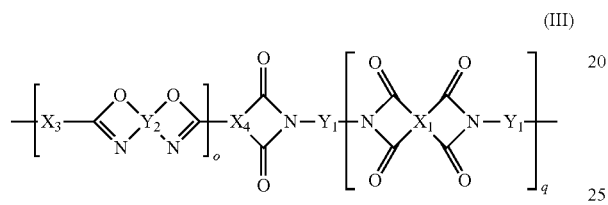

(III)

wherein $X_1$ is selected from the group consisting of

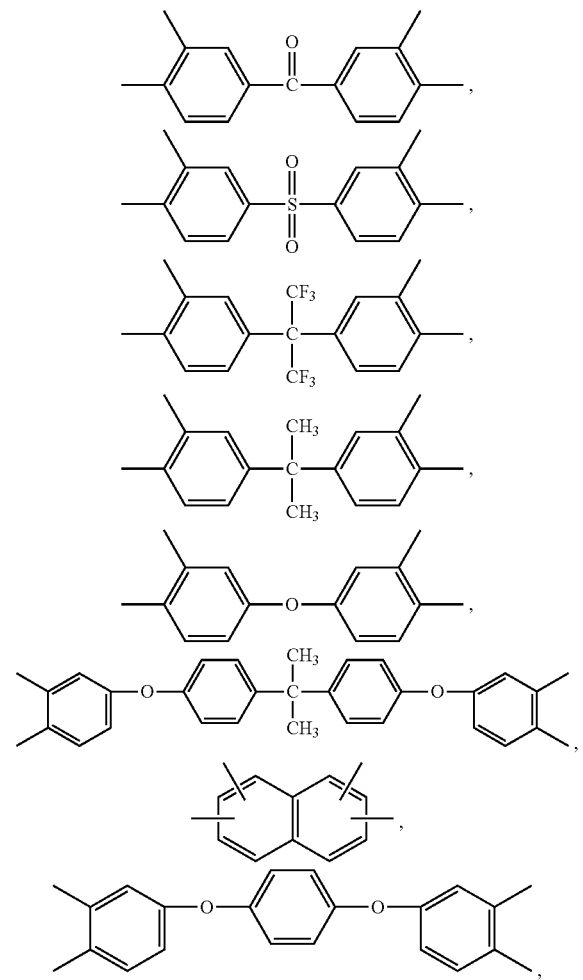

and mixtures thereof; wherein $X_3$ is selected from the group consisting of

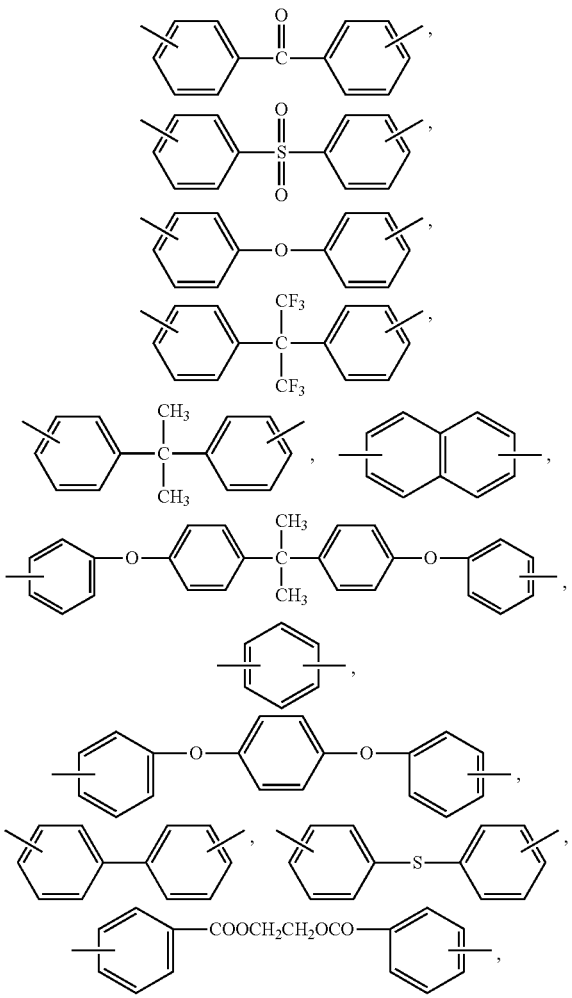

-continued

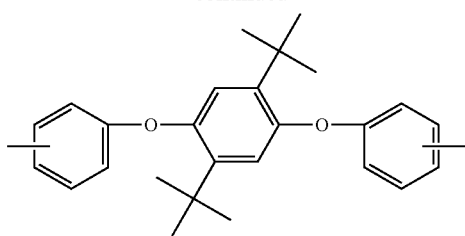

and mixtures thereof; wherein $X_4$ is selected from the group consisting of

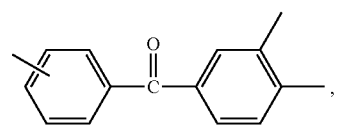

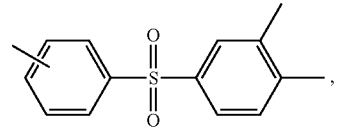

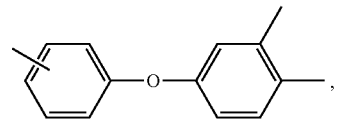

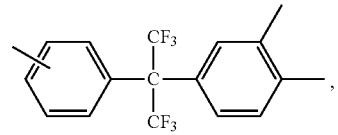

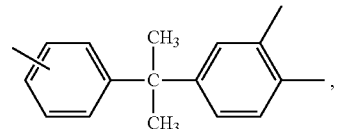

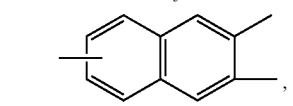

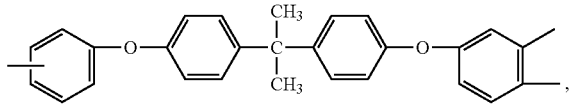

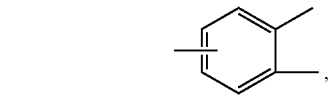

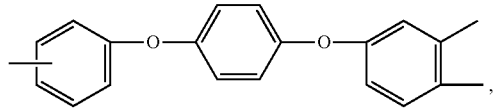

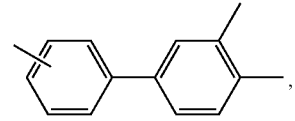

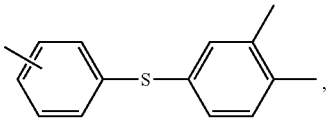

-continued

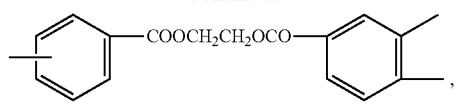

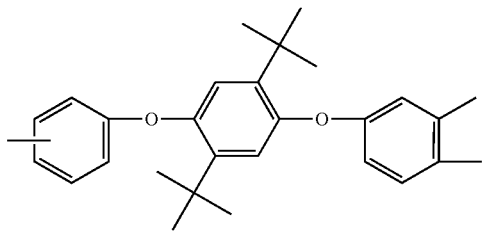

and mixtures thereof; $Y_1$ is selected from the group consisting of

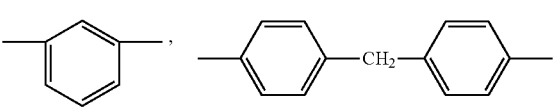

and mixtures thereof; $Y_2$ is selected from the group consisting of

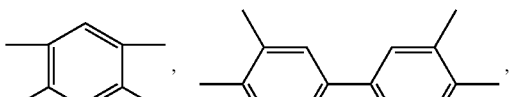

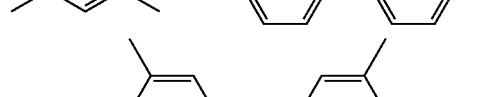

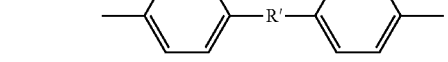

and mixtures thereof, and —R'— is selected from the group consisting of

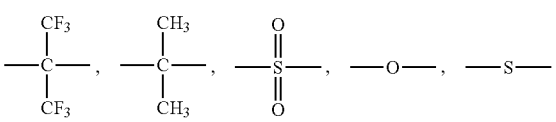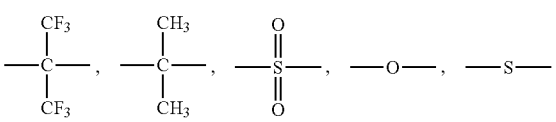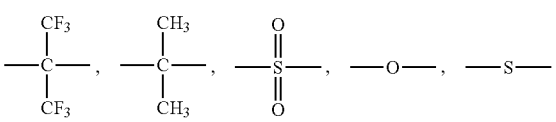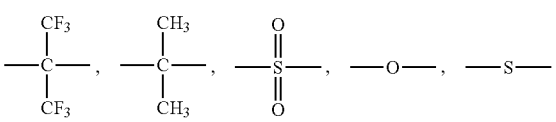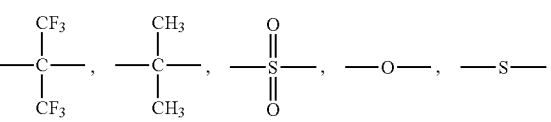

and mixtures thereof; o and q are independent integers from 2 to 500: contacting the mixture of gases to one side of the polybenzoxazole membrane of formula (III) to cause at least one gas to permeate said membrane; and removing from an opposite side of said polybenzoxazole membrane of formula (III) a permeate gas composition comprising a portion of said at least one gas that permeated said membrane, wherein said polybenzoxazole membrane of formula (III) is derived from a self-cross-linkable aromatic polyimide polymer obtained from hydroxyl- and carboxylic acid-containing aromatic diamines.

2. The process of claim 1 wherein in said formula (III), $X_1$ is selected from the group consisting of

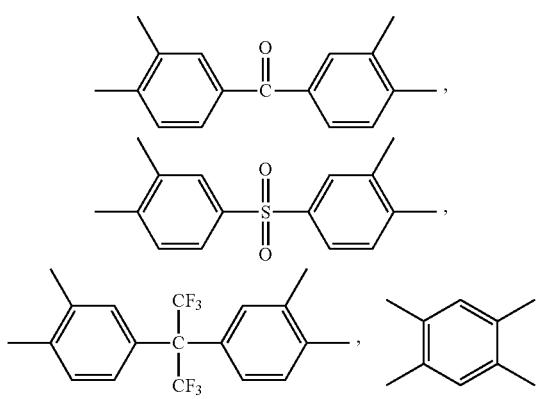

and mixtures thereof.

3. The process of claim 1 wherein in said formula (III), X3 is selected from the group consisting of

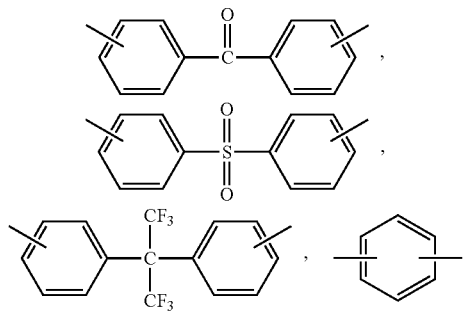

and mixtures thereof.

4. The process of claim 1 wherein in said formula (III), $X_4$ is selected from the group consisting of

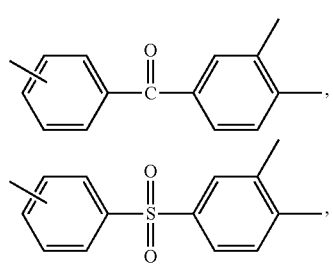

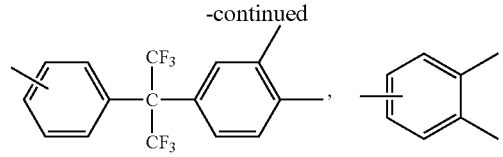

and mixtures thereof.

5. The process of claim 1 wherein in said formula (III), $Y_1$ is

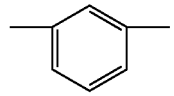

6. The process of claim 1 wherein $Y_2$ is selected from the group consisting of

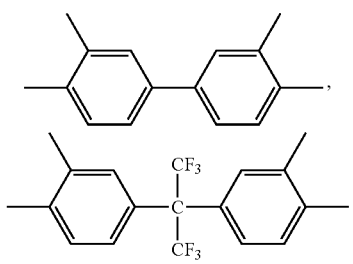

and mixtures thereof.

7. The process of claim 1 wherein said mixture of gases comprises a mixture of carbon dioxide and methane.

8. The process of claim 1 wherein said mixture of gases comprises a mixture of hydrogen and methane.

9. The process of claim 1 wherein said mixture of gases comprises a mixture of helium and methane.

10. The process of claim 1 wherein said mixture of gases comprises a mixture of at least one volatile organic compound and at least one atmospheric gas.

11. The process of claim 1 wherein said mixture of gases comprises nitrogen and hydrogen.

12. The process of claim 1 wherein said mixture of gases comprises a mixture of carbon dioxide, oxygen, nitrogen, water vapor, hydrogen sulfide, helium and methane.

13. The process of claim 1 wherein said mixture of gases comprises a mixture of paraffins and olefins.

* * * * *